United States Patent [19]
Magota et al.

[11] Patent Number: 5,885,821
[45] Date of Patent: Mar. 23, 1999

[54] PROCESS FOR PRODUCTION OF SECRETORY KEX2 DERIVATIVES

[75] Inventors: Koji Magota, Takatsuki; Toyofumi Masuda, Ibaraki; Yuji Suzuki, Ashikaga; Masayuki Yabuta, Tatebayashi, all of Japan

[73] Assignee: Suntory Limited, Osaka, Japan

[21] Appl. No.: 805,918

[22] Filed: Mar. 4, 1997

[30] Foreign Application Priority Data

Mar. 4, 1996 [JP] Japan ................................. 8-073217
Dec. 16, 1996 [JP] Japan ................................. 8-352580

[51] Int. Cl.$^6$ .............................. C12N 9/60; C12N 1/19; C12N 15/57
[52] U.S. Cl. ...................... 435/224; 435/254.2; 536/23.2
[58] Field of Search .................... 435/224, 219, 435/254.2, 320.1; 536/23.2

[56] References Cited

U.S. PATENT DOCUMENTS 5,162,220  11/1992  Oshima et al. ......................... 435/224

OTHER PUBLICATIONS

Charles Brenner et al., "Structural And Enzymatic Characterization Of A Purified Prohormone–Processing Enzyme; Secreted, Soluble Kex2 Protease", *Proc. Nat'l. Academy Sci. USA*, vol. 89, pp. 922–926, (1992).

Doris Germain et al., "Expression Of The Saccharomyces Cerevisiae Kex2p Endoprotease In Insect Cells Evidence For A Carboxy–Terminal Autoprocessing Event", *Eur. J. Biochem*, vol. 204, 121–126 (1992).

Peter G. Seebooth, "In–vitro Cleavage Of a Fusion Protein Bound To Cellulose Using The Soluble yscFs (Kex2) Variant", *Appl. Microbiol Biotechnol*, vol. 37, 621–625, (1992).

*Primary Examiner*—Keith D. Hendricks
*Attorney, Agent, or Firm*—Burns, Doane, Swecker & Mathis, L.L.P.

[57] ABSTRACT

Kex2 protease derivatives obtained by transforming methanol-assimilating with expression vectors containing DNA coding for any amino acid sequence which is an amino acid sequence of Kex2 protease wherein the N-terminus is the Met at position 1 and the C-terminus is one of the amino acids between positions 618 (inclusive) and 698 (inclusive), or a modification of that amino acid sequence, culturing the resulting transformants and recovering the derivatives from the cultures, as well as gene systems coding for the derivatives and a method for producing the Kex2 protease derivatives using the gene systems. Also, a method for excision of desired peptides using the Kex2 protease derivatives.

7 Claims, 27 Drawing Sheets

Fig.1

```
                  U1                                      U2
5' AATTCATGAAATCTGTTAAAAAGCGTTCTGTTTCTGAAAT TCAGCTGATGCATAACCTGG
3'      GTACTTTAGACAATTTTTCGCAAGACAAAGACTTTAAGTCGACTAC GTATTGGACC
                         L7                 U3

GCAAACACCTGAATAGCATGG AACGGCGTCGAGTGGCTGCGTAAGAAACTGCAGGACGTCC
   CGTTTGTGGACTTATCGTACC TTGCGCAGCT CACCGACGCATTCTTTGACGTCCTGCAGG
                 L6       U4                                 L5   U5

AC AACTTCGTTGCGCTGGGTGCACCGCTGGCTCCACGTGATGC AGGATCCCAACGTCCGC
TGTTGAAGCAAC GCGACCCACGTGGCGACCGAGGTGCACTACGTCCTAGGGTT GCAGGCG
                        L4                                  U6

GTAAGAAAGAAGATAACGTACT GGTTGAATCTCATGAGAAATCCCTGGGCGAAGCTGACA
CATTCTTTCTTCTATTGCATGA CCAACTTAGAG TACTCTTTAGGGACCCGCTTCGACTGT
         L3                 U7                              L2

AA GCCCGATGTGTTAACGTGCTGACCAAAGCCGAAAAGCCAGTAAG            3'
   TTCGGCTACACAATT GCACGACTGGTTTCGCTTTTCGGTCATTCAGCT        5'
                                                  L1
```

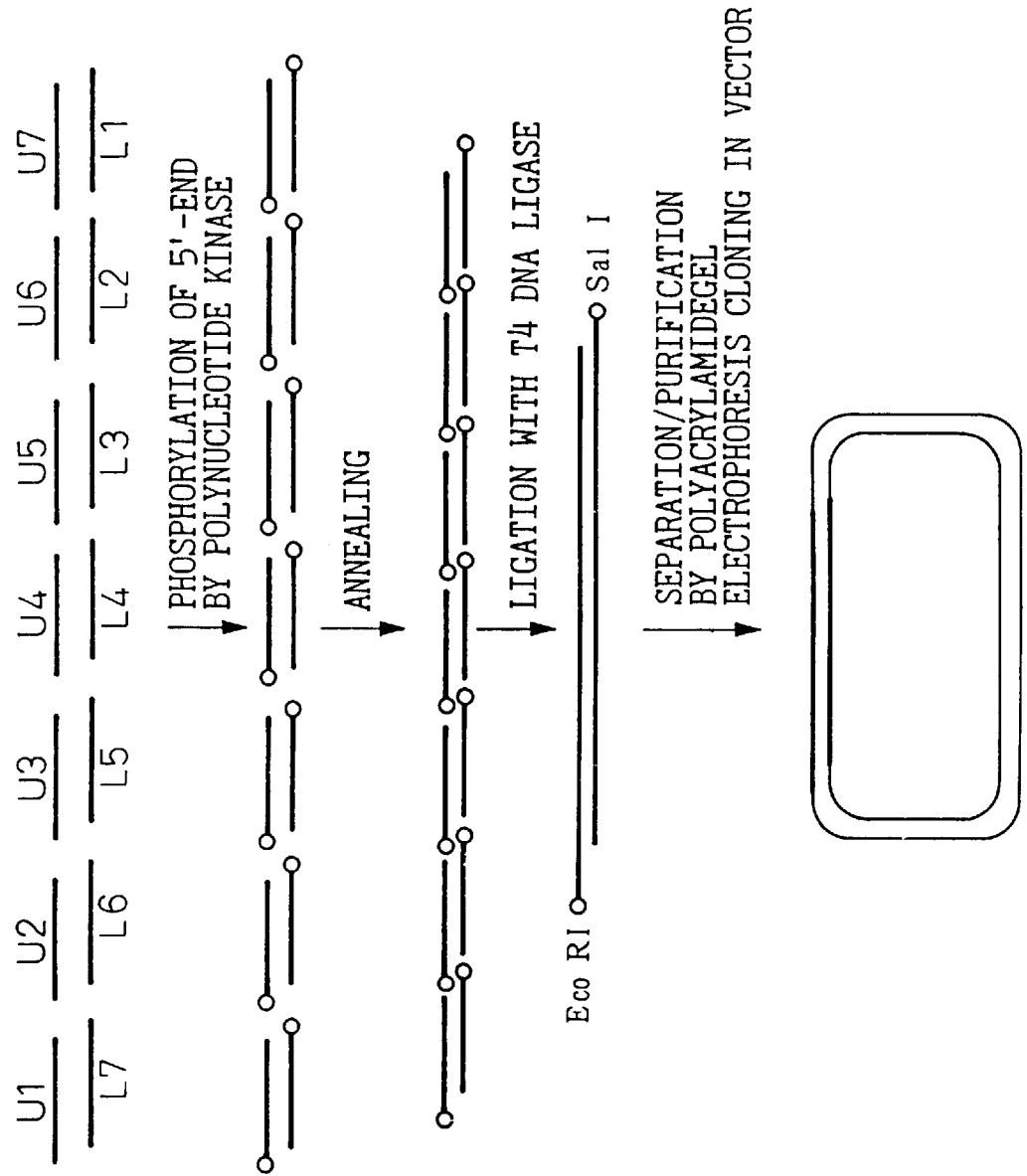

Fig. 4
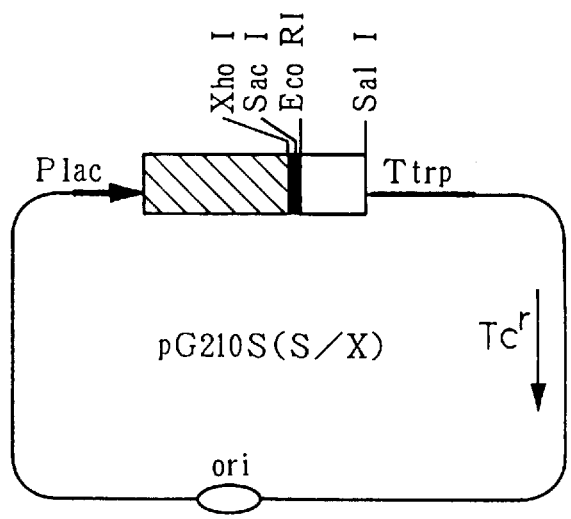
↓ Sac I/Xho I
↓ Exo III NUCLEASE
↓ MUNGBEAN NUCLEASE
↓ DNA POLYMERASE (KLENOW FRAGMENT)
↓ T4 DNA LIGASE
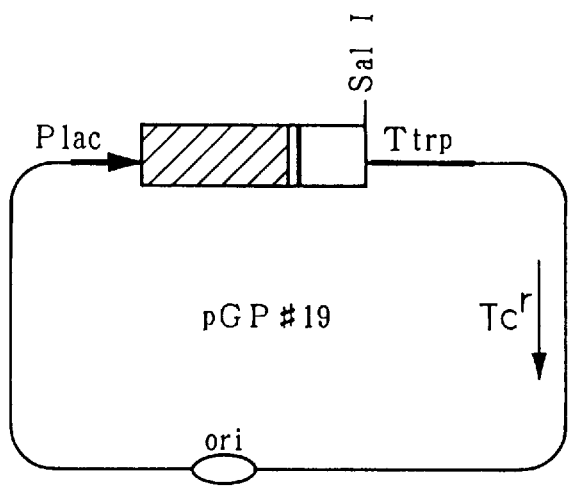

CAT-PTH (1-34) EXPRESSION AND PURIFICATION OF CHIMERIC PROTEIN

1. MOLECULAR WEIGHT MARKER
2. SOLUBLE FRACTION AFTER CELL DISRUPTION
3. CAT-PTH (1-34) CHIMERIC PROTEIN AFTER PURIFICATION

Fig. 21
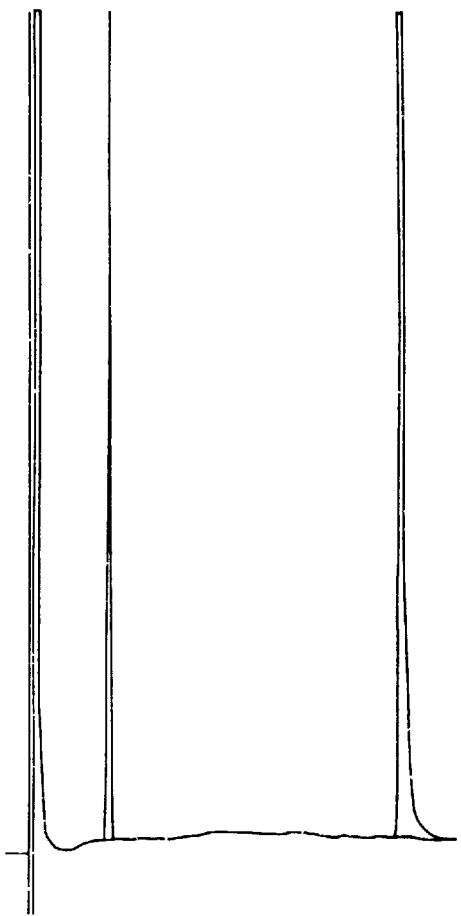
PEAKS BEFORE
Kex2-660 TREATMENT
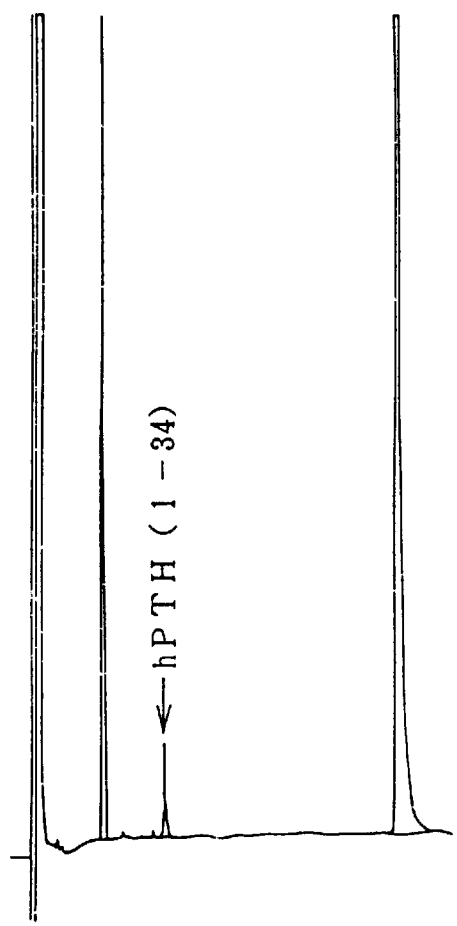
PEAKS AFTER
Kex2-660 TREATMENT
← hPTH (1-34)

10% SDS-PAGE 5 μl CULTURE SUPERNATANT/LANE

SEQUENCE LISTING ( 1 ) GENERAL INFORMATION:

( i i i ) NUMBER OF SEQUENCES: 45

( 2 ) INFORMATION FOR SEQ ID NO:1:

( i ) SEQUENCE CHARACTERISTICS:
        ( A ) LENGTH: 2848 base pairs
        ( B ) TYPE: nucleic acid
        ( C ) STRANDEDNESS: double
        ( D ) TOPOLOGY: linear ( i i ) MOLECULE TYPE: cDNA ( v i ) ORIGINAL SOURCE:
        ( A ) ORGANISM: Saccharomyces cerevisiae
        ( B ) STRAIN: X2180-IB ( i x ) FEATURE:
        ( A ) NAME/KEY: CDS
        ( B ) LOCATION: 170..2611

( x i ) SEQUENCE DESCRIPTION: SEQ ID NO:1:

```
TGCATAATTC  TGTCATAAGC  CTGTTCTTTT  TCCTGGCTTA  AACATCCCGT  TTTGTAAAAG     60

AGAAATCTAT  TCCACATATT  TCATTCATTC  GGCTACCATA  CTAAGGATAA  ACTAATCCCG    120

TTGTTTTTTG  GCCTCGTCAC  ATAATTATAA  ACTACTAACC  CATTATCAG ATG AAA         175
                                                         Met Lys
                                                           1

GTG AGG AAA TAT ATT ACT TTA TGC TTT TGG TGG GCC TTT TCA ACA TCC          223
Val Arg Lys Tyr Ile Thr Leu Cys Phe Trp Trp Ala Phe Ser Thr Ser
          5               10                  15

GCT CTT GTA TCA TCA CAA CAA ATT CCA TTG AAG GAC CAT ACG TCA CGA          271
Ala Leu Val Ser Ser Gln Gln Ile Pro Leu Lys Asp His Thr Ser Arg
      20              25                  30

CAG TAT TTT GCT GTA GAA AGC AAT GAA ACA TTA TCC CGC TTG GAG GAA          319
Gln Tyr Phe Ala Val Glu Ser Asn Glu Thr Leu Ser Arg Leu Glu Glu
 35              40                  45                  50

ATG CAT CCA AAT TGG AAA TAT GAA CAT GAT GTT CGA GGG CTA CCA AAC          367
Met His Pro Asn Trp Lys Tyr Glu His Asp Val Arg Gly Leu Pro Asn
                  55                  60                  65

CAT TAT GTT TTT TCA AAA GAG TTG CTA AAA TTG GGC AAA AGA TCA TCA          415
His Tyr Val Phe Ser Lys Glu Leu Leu Lys Leu Gly Lys Arg Ser Ser
              70                  75                  80

TTA GAA GAG TTA CAG GGG GAT AAC AAC GAC CAC ATA TTA TCT GTC CAT          463
Leu Glu Glu Leu Gln Gly Asp Asn Asn Asp His Ile Leu Ser Val His
          85                  90                  95

GAT TTA TTC CCG CGT AAC GAC CTA TTT AAG AGA CTA CCG GTG CCT GCT          511
Asp Leu Phe Pro Arg Asn Asp Leu Phe Lys Arg Leu Pro Val Pro Ala
     100                 105                 110

CCA CCA ATG GAC TCA AGC TTG TTA CCG GTA AAA GAA GCT GAG GAT AAA          559
```

```
Pro  Pro  Met  Asp  Ser  Ser  Leu  Leu  Pro  Val  Lys  Glu  Ala  Glu  Asp  Lys
115                 120                      125                      130

CTC  AGC  ATA  AAT  GAT  CCG  CTT  TTT  GAG  AGG  CAG  TGG  CAC  TTG  GTC  AAT      607
Leu  Ser  Ile  Asn  Asp  Pro  Leu  Phe  Glu  Arg  Gln  Trp  His  Leu  Val  Asn
                    135                      140                      145

CCA  AGT  TTT  CCT  GGC  AGT  GAT  ATA  AAT  GTT  CTT  GAT  CTG  TGG  TAC  AAT      655
Pro  Ser  Phe  Pro  Gly  Ser  Asp  Ile  Asn  Val  Leu  Asp  Leu  Trp  Tyr  Asn
               150                      155                      160

AAT  ATT  ACA  GGC  GCA  GGG  GTC  GTG  GCT  GCC  ATT  GTT  GAT  GAT  GGC  CTT      703
Asn  Ile  Thr  Gly  Ala  Gly  Val  Val  Ala  Ala  Ile  Val  Asp  Asp  Gly  Leu
          165                      170                      175

GAC  TAC  GAA  AAT  GAA  GAC  TTG  AAG  GAT  AAT  TTT  TGC  GCT  GAA  GGT  TCT      751
Asp  Tyr  Glu  Asn  Glu  Asp  Leu  Lys  Asp  Asn  Phe  Cys  Ala  Glu  Gly  Ser
     180                      185                      190

TGG  GAT  TTC  AAC  GAC  AAT  ACC  AAT  TTA  CCT  AAA  CCA  AGA  TTA  TCT  GAT      799
Trp  Asp  Phe  Asn  Asp  Asn  Thr  Asn  Leu  Pro  Lys  Pro  Arg  Leu  Ser  Asp
195                      200                      205                      210

GAC  TAC  CAT  GGT  ACG  AGA  TGT  GCA  GGT  GAA  ATA  GCT  GCC  AAA  AAA  GGT      847
Asp  Tyr  His  Gly  Thr  Arg  Cys  Ala  Gly  Glu  Ile  Ala  Ala  Lys  Lys  Gly
                    215                      220                      225

AAC  AAT  TTT  TGC  GGT  GTC  GGG  GTA  GGT  TAC  AAC  GCT  AAA  ATC  TCA  GGC      895
Asn  Asn  Phe  Cys  Gly  Val  Gly  Val  Gly  Tyr  Asn  Ala  Lys  Ile  Ser  Gly
               230                      235                      240

ATA  AGA  ATC  TTA  TCC  GGT  GAT  ATC  ACT  ACG  GAA  GAT  GAA  GCT  GCG  TCC      943
Ile  Arg  Ile  Leu  Ser  Gly  Asp  Ile  Thr  Thr  Glu  Asp  Glu  Ala  Ala  Ser
          245                      250                      255

TTG  ATT  TAT  GGT  CTA  GAC  GTA  AAC  GAT  ATA  TAT  TCA  TGC  TCA  TGG  GGT      991
Leu  Ile  Tyr  Gly  Leu  Asp  Val  Asn  Asp  Ile  Tyr  Ser  Cys  Ser  Trp  Gly
     260                      265                      270

CCC  GCT  GAT  GAC  GGA  AGA  CAT  TTA  CAA  GGC  CCT  AGT  GAC  CTG  GTG  AAA     1039
Pro  Ala  Asp  Asp  Gly  Arg  His  Leu  Gln  Gly  Pro  Ser  Asp  Leu  Val  Lys
275                      280                      285                      290

AAG  GCT  TTA  GTA  AAA  GGT  GTT  ACT  GAG  GGA  AGA  GAT  TCC  AAA  GGA  GCG     1087
Lys  Ala  Leu  Val  Lys  Gly  Val  Thr  Glu  Gly  Arg  Asp  Ser  Lys  Gly  Ala
                    295                      300                      305

ATT  TAC  GTT  TTT  GCC  AGT  GGA  AAT  GGT  GGA  ACT  CGT  GGT  GAT  AAT  TGC     1135
Ile  Tyr  Val  Phe  Ala  Ser  Gly  Asn  Gly  Gly  Thr  Arg  Gly  Asp  Asn  Cys
               310                      315                      320

AAT  TAC  GAC  GGC  TAT  ACT  AAT  TCC  ATA  TAT  TCT  ATT  ACT  ATT  GGG  GCT     1183
Asn  Tyr  Asp  Gly  Tyr  Thr  Asn  Ser  Ile  Tyr  Ser  Ile  Thr  Ile  Gly  Ala
          325                      330                      335

ATT  GAT  CAC  AAA  GAT  CTA  CAT  CCT  CCT  TAT  TCC  GAA  GGT  TGT  TCC  GCC     1231
Ile  Asp  His  Lys  Asp  Leu  His  Pro  Pro  Tyr  Ser  Glu  Gly  Cys  Ser  Ala
     340                      345                      350

GTC  ATG  GCA  GTC  ACG  TAT  TCT  TCA  GGT  TCA  GGC  GAA  TAT  ATT  CAT  TCG     1279
Val  Met  Ala  Val  Thr  Tyr  Ser  Ser  Gly  Ser  Gly  Glu  Tyr  Ile  His  Ser
355                      360                      365                      370

AGT  GAT  ATC  AAC  GGC  AGA  TGC  AGT  AAT  AGC  CAC  GGT  GGA  ACG  TCT  GCG     1327
Ser  Asp  Ile  Asn  Gly  Arg  Cys  Ser  Asn  Ser  His  Gly  Gly  Thr  Ser  Ala
                    375                      380                      385

GCT  GCT  CCA  TTA  GCT  GCC  GGT  GTT  TAC  ACT  TTG  TTA  CTA  GAA  GCC  AAC     1375
Ala  Ala  Pro  Leu  Ala  Ala  Gly  Val  Tyr  Thr  Leu  Leu  Leu  Glu  Ala  Asn
               390                      395                      400

CCA  AAC  CTA  ACT  TGG  AGA  GAC  GTA  CAG  TAT  TTA  TCA  ATC  TTG  TCT  GCG     1423
Pro  Asn  Leu  Thr  Trp  Arg  Asp  Val  Gln  Tyr  Leu  Ser  Ile  Leu  Ser  Ala
          405                      410                      415

GTA  GGG  TTA  GAA  AAG  AAC  GCT  GAC  GGA  GAT  TGG  AGA  GAT  AGC  GCC  ATG     1471
Val  Gly  Leu  Glu  Lys  Asn  Ala  Asp  Gly  Asp  Trp  Arg  Asp  Ser  Ala  Met
     420                      425                      430

GGG  AAG  AAA  TAC  TCT  CAT  CGC  TAT  GGC  TTT  GGT  AAA  ATC  GAT  GCC  CAT     1519
```

|     |     |     |     |     |     |     |     |     |     |     |     |     |     |     |      |
|-----|-----|-----|-----|-----|-----|-----|-----|-----|-----|-----|-----|-----|-----|-----|------|
| Gly | Lys | Lys | Tyr | Ser | His | Arg | Tyr | Gly | Phe | Gly | Lys | Ile | Asp | Ala | His  |
| 435 |     |     |     | 440 |     |     |     |     | 445 |     |     |     |     | 450 |      |
| AAG | TTA | ATT | GAA | ATG | TCC | AAG | ACC | TGG | GAG | AAT | GTT | AAC | GCA | CAA | ACC  | 1567 |
| Lys | Leu | Ile | Glu | Met | Ser | Lys | Thr | Trp | Glu | Asn | Val | Asn | Ala | Gln | Thr  |
|     |     |     |     | 455 |     |     |     | 460 |     |     |     |     | 465 |     |      |
| TGG | TTT | TAC | CTG | CCA | ACA | TTG | TAT | GTT | TCC | CAG | TCC | ACA | AAC | TCC | ACG  | 1615 |
| Trp | Phe | Tyr | Leu | Pro | Thr | Leu | Tyr | Val | Ser | Gln | Ser | Thr | Asn | Ser | Thr  |
|     |     |     | 470 |     |     |     | 475 |     |     |     |     | 480 |     |     |      |
| GAA | GAG | ACA | TTA | GAA | TCC | GTC | ATA | ACC | ATA | TCA | GAA | AAA | AGT | CTT | CAA  | 1663 |
| Glu | Glu | Thr | Leu | Glu | Ser | Val | Ile | Thr | Ile | Ser | Glu | Lys | Ser | Leu | Gln  |
|     |     | 485 |     |     |     |     | 490 |     |     |     |     | 495 |     |     |      |
| GAT | GCT | AAC | TTC | AAG | AGA | ATT | GAG | CAC | GTC | ACG | GTA | ACT | GTA | GAT | ATT  | 1711 |
| Asp | Ala | Asn | Phe | Lys | Arg | Ile | Glu | His | Val | Thr | Val | Thr | Val | Asp | Ile  |
|     | 500 |     |     |     |     | 505 |     |     |     |     | 510 |     |     |     |      |
| GAT | ACA | GAA | ATT | AGG | GGA | ACT | ACG | ACT | GTC | GAT | TTA | ATA | TCA | CCA | GCG  | 1759 |
| Asp | Thr | Glu | Ile | Arg | Gly | Thr | Thr | Thr | Val | Asp | Leu | Ile | Ser | Pro | Ala  |
| 515 |     |     |     | 520 |     |     |     |     | 525 |     |     |     |     | 530 |      |
| GGG | ATA | ATT | TCA | AAC | CTT | GGC | GTT | GTA | AGA | CCA | AGA | GAT | GTT | TCA | TCA  | 1807 |
| Gly | Ile | Ile | Ser | Asn | Leu | Gly | Val | Val | Arg | Pro | Arg | Asp | Val | Ser | Ser  |
|     |     |     |     | 535 |     |     |     |     | 540 |     |     |     |     | 545 |      |
| GAG | GGA | TTC | AAA | GAC | TGG | ACA | TTC | ATG | TCT | GTA | GCA | CAT | TGG | GGT | GAG  | 1855 |
| Glu | Gly | Phe | Lys | Asp | Trp | Thr | Phe | Met | Ser | Val | Ala | His | Trp | Gly | Glu  |
|     |     |     | 550 |     |     |     |     | 555 |     |     |     |     | 560 |     |      |
| AAC | GGC | GTA | GGT | GAT | TGG | AAA | ATC | AAG | GTT | AAG | ACA | ACA | GAA | AAT | GGA  | 1903 |
| Asn | Gly | Val | Gly | Asp | Trp | Lys | Ile | Lys | Val | Lys | Thr | Thr | Glu | Asn | Gly  |
|     |     | 565 |     |     |     |     | 570 |     |     |     |     | 575 |     |     |      |
| CAC | AGG | ATT | GAC | TTC | CAC | AGT | TGG | AGG | CTG | AAG | CTC | TTT | GGG | GAA | TCC  | 1951 |
| His | Arg | Ile | Asp | Phe | His | Ser | Trp | Arg | Leu | Lys | Leu | Phe | Gly | Glu | Ser  |
|     | 580 |     |     |     |     | 585 |     |     |     |     | 590 |     |     |     |      |
| ATT | GAT | TCA | TCT | AAA | ACA | GAA | ACT | TTC | GTC | TTT | GGA | AAC | GAT | AAA | GAG  | 1999 |
| Ile | Asp | Ser | Ser | Lys | Thr | Glu | Thr | Phe | Val | Phe | Gly | Asn | Asp | Lys | Glu  |
| 595 |     |     |     |     | 600 |     |     |     |     | 605 |     |     |     |     | 610  |
| GAG | GTT | GAA | CCA | GCT | GCT | ACA | GAA | AGT | ACC | GTA | TCA | CAA | TAT | TCT | GCC  | 2047 |
| Glu | Val | Glu | Pro | Ala | Ala | Thr | Glu | Ser | Thr | Val | Ser | Gln | Tyr | Ser | Ala  |
|     |     |     |     | 615 |     |     |     |     | 620 |     |     |     |     | 625 |      |
| AGT | TCA | ACT | TCT | ATT | TCC | ATC | AGC | GCT | ACT | TCT | ACA | TCT | TCT | ATC | TCA  | 2095 |
| Ser | Ser | Thr | Ser | Ile | Ser | Ile | Ser | Ala | Thr | Ser | Thr | Ser | Ser | Ile | Ser  |
|     |     |     | 630 |     |     |     |     | 635 |     |     |     |     | 640 |     |      |
| ATT | GGT | GTG | GAA | ACG | TCG | GCC | ATT | CCC | CAA | ACG | ACT | ACT | GCG | AGT | ACC  | 2143 |
| Ile | Gly | Val | Glu | Thr | Ser | Ala | Ile | Pro | Gln | Thr | Thr | Thr | Ala | Ser | Thr  |
|     |     | 645 |     |     |     |     | 650 |     |     |     |     | 655 |     |     |      |
| GAT | CCT | GAT | TCT | GAT | CCA | AAC | ACT | CCT | AAA | AAA | CTT | TCC | TCT | CCT | AGG  | 2191 |
| Asp | Pro | Asp | Ser | Asp | Pro | Asn | Thr | Pro | Lys | Lys | Leu | Ser | Ser | Pro | Arg  |
|     | 660 |     |     |     |     | 665 |     |     |     |     | 670 |     |     |     |      |
| CAA | GCC | ATG | CAT | TAT | TTT | TTA | ACA | ATA | TTT | TTG | ATT | GGC | GCC | ACA | TTT  | 2239 |
| Gln | Ala | Met | His | Tyr | Phe | Leu | Thr | Ile | Phe | Leu | Ile | Gly | Ala | Thr | Phe  |
| 675 |     |     |     |     | 680 |     |     |     |     | 685 |     |     |     |     | 690  |
| TTG | GTG | TTA | TAC | TTC | ATG | TTT | TTT | ATG | AAA | TCA | AGG | AGA | AGG | ATC | AGA  | 2287 |
| Leu | Val | Leu | Tyr | Phe | Met | Phe | Phe | Met | Lys | Ser | Arg | Arg | Arg | Ile | Arg  |
|     |     |     |     | 695 |     |     |     |     | 700 |     |     |     |     | 705 |      |
| AGG | TCA | AGA | GCG | GAA | ACG | TAT | GAA | TTC | GAT | ATC | ATT | GAT | ACA | GAC | TCT  | 2335 |
| Arg | Ser | Arg | Ala | Glu | Thr | Tyr | Glu | Phe | Asp | Ile | Ile | Asp | Thr | Asp | Ser  |
|     |     |     | 710 |     |     |     |     | 715 |     |     |     |     | 720 |     |      |
| GAG | TAC | GAT | TCT | ACT | TTG | GAC | AAT | GGA | ACT | TCC | GGA | ATT | ACT | GAG | CCC  | 2383 |
| Glu | Tyr | Asp | Ser | Thr | Leu | Asp | Asn | Gly | Thr | Ser | Gly | Ile | Thr | Glu | Pro  |
|     |     | 725 |     |     |     |     | 730 |     |     |     |     | 735 |     |     |      |
| GAA | GAG | GTT | GAG | GAC | TTC | GAT | TTT | GAT | TTG | TCC | GAT | GAA | GAC | CAT | CTT  | 2431 |
| Glu | Glu | Val | Glu | Asp | Phe | Asp | Phe | Asp | Leu | Ser | Asp | Glu | Asp | His | Leu  |
|     |     | 740 |     |     |     |     | 745 |     |     |     |     | 750 |     |     |      |
| GCA | AGT | TTG | TCT | TCA | TCA | GAA | AAC | GGT | GAT | GCT | GAA | CAT | ACA | ATT | GAT  | 2479 |

```
Ala  Ser  Leu  Ser  Ser  Ser  Glu  Asn  Gly  Asp  Ala  Glu  His  Thr  Ile  Asp
755                 760                 765                           770

AGT  GTA  CTA  ACA  AAC  GAA  AAT  CCA  TTT  AGT  GAC  CCT  ATA  AAG  CAA  AAG        2527
Ser  Val  Leu  Thr  Asn  Glu  Asn  Pro  Phe  Ser  Asp  Pro  Ile  Lys  Gln  Lys
               775                 780                           785

TTC  CCA  AAT  GAC  GCC  AAC  GCA  GAA  TCT  GCT  TCC  AAT  AAA  TTA  CAA  GAA        2575
Phe  Pro  Asn  Asp  Ala  Asn  Ala  Glu  Ser  Ala  Ser  Asn  Lys  Leu  Gln  Glu
               790                 795                           800

TTA  CAG  CCT  GAT  GTT  CCT  CCA  TCT  TCC  GGA  CGA  TCG  TGATTCGATA                 2621
Leu  Gln  Pro  Asp  Val  Pro  Pro  Ser  Ser  Gly  Arg  Ser
               805                 810

TGTACAGAAA  GCTTCAAATT  ACAAATAGC  ATTTTTTCT  TATAGATTAT  AATACTCTCT                   2681

CATACGTATA  CGTATATGTG  TATATGATAT  ATAAACAAAC  ATTAATATCC  TATTCCTTCC                 2741

GTTTGAAATC  CCTATGATGT  ACTTTGCATT  GTTTGCACCC  GCGAATAAAA  TGAAAACTCC                 2801

GAACCGATAT  ATCAAGCACA  TAAAAGGGGA  GGGTCCAATT  AATGCAT                                2848
```

(2) INFORMATION FOR SEQ ID NO:2:

(i) SEQUENCE CHARACTERISTICS:
        (A) LENGTH: 139 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

```
Thr  Met  Ile  Thr  Asp  Ser  Leu  Ala  Val  Val  Leu  Gln  Arg  Arg  Asp  Trp
1                   5                   10                           15

Glu  Asn  Pro  Gly  Val  Thr  Gln  Leu  Asn  Arg  Leu  Ala  Ala  His  Pro  Pro
               20                  25                           30

Phe  Ala  Ser  Trp  Arg  Asn  Ser  Glu  Glu  Ala  Arg  Thr  Asp  Arg  Pro  Ser
               35                  40                           45

Gln  Gln  Leu  Arg  Ser  Leu  Asn  Gly  Glu  Trp  Arg  Phe  Ala  Trp  Phe  Pro
               50                  55                           60

Ala  Pro  Glu  Ala  Val  Pro  Glu  Ser  Leu  Leu  Glu  Ser  Asp  Leu  Pro  Glu
65                  70                  75                               80

Ala  Asp  Thr  Val  Val  Pro  Ser  Asn  Trp  Gln  Met  His  Gly  Tyr  Asp
                    85                  90                           95

Ala  Pro  Ile  Tyr  Thr  Asn  Val  Thr  Tyr  Pro  Ile  Thr  Val  Asn  Pro  Pro
               100                 105                          110

Phe  Val  Pro  Thr  Glu  Asn  Pro  Thr  Gly  Ser  Tyr  Ser  Leu  Thr  Phe  Asn
               115                 120                          125

Val  Asp  Glu  Ser  Trp  Leu  Gln  Glu  Gly  Gln  Thr
               130                 135
```

(2) INFORMATION FOR SEQ ID NO:3:

(i) SEQUENCE CHARACTERISTICS:
        (A) LENGTH: 84 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

```
Ser  Val  Ser  Glu  Ile  Gln  Leu  Met  His  Asn  Leu  Gly  Lys  His  Leu  Asn
1                   5                   10                           15

Ser  Met  Glu  Arg  Val  Glu  Trp  Leu  Arg  Lys  Lys  Leu  Gln  Asp  Val  His
```

|  | 20 | 25 | 30 |
| --- | --- | --- | --- |

Asn Phe Val Ala Leu Gly Ala Pro Leu Ala Pro Arg Asp Ala Gly Ser
        35                      40                      45

Gln Arg Pro Arg Lys Lys Glu Asp Asn Val Leu Val Glu Ser His Glu
    50                      55                      60

Lys Ser Leu Gly Glu Ala Asp Lys Ala Asp Val Asn Val Leu Thr Lys
65                      70                      75                      80

Ala Lys Ser Gln ( 2 ) INFORMATION FOR SEQ ID NO:4:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

Gly Gly Ser Ser Arg Val Ile Leu Gln Ala Cys Leu Ile Asn
1               5                       10

( 2 ) INFORMATION FOR SEQ ID NO:5:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "synthetic DNA"

( x i ) SEQUENCE DESCRIPTION: SEQ ID NO:5:

AATTCATGAA ATCTGTTAAA AAGCGTTCTG TTTCTGAAAT    40

( 2 ) INFORMATION FOR SEQ ID NO:6:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "synthetic DNA"

( x i ) SEQUENCE DESCRIPTION: SEQ ID NO:6:

TCAGCTGATG CATAACCTGG GCAAACACCT GAATAGCATG G    41

( 2 ) INFORMATION FOR SEQ ID NO:7:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "synthetic DNA"

( x i ) SEQUENCE DESCRIPTION: SEQ ID NO:7:

AACGCGTCGA GTGGCTGCGT AAGAAACTGC AGGACGTCCA C    41

( 2 ) INFORMATION FOR SEQ ID NO:8:

( i ) SEQUENCE CHARACTERISTICS:
    ( A ) LENGTH: 41 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "synthetic DNA"

( x i ) SEQUENCE DESCRIPTION: SEQ ID NO:8:

AACTTCGTTG CGCTGGGTGC ACCGCTGGCT CCACGTGATG C    41

( 2 ) INFORMATION FOR SEQ ID NO:9:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "synthetic DNA"

( x i ) SEQUENCE DESCRIPTION: SEQ ID NO:9:

AGGATCCCAA CGTCCGCGTA AGAAAGAAGA TAACGTACT    39

( 2 ) INFORMATION FOR SEQ ID NO:10:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "synthetic DNA"

( x i ) SEQUENCE DESCRIPTION: SEQ ID NO:10:

GGTTGAATCT CATGAGAAAT CCCTGGGCGA AGCTGACAAA    40

( 2 ) INFORMATION FOR SEQ ID NO:11:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "synthetic DNA"

( x i ) SEQUENCE DESCRIPTION: SEQ ID NO:11:

GCCGATGTTA ACGTGCTGAC CAAAGCGAAA AGCCAGTAAG    40

( 2 ) INFORMATION FOR SEQ ID NO:12:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "synthetic DNA"

( x i ) SEQUENCE DESCRIPTION: SEQ ID NO:12:

TCGACTTACT GGCTTTTCGC TTTGGTCAGC ACG    33

( 2 ) INFORMATION FOR SEQ ID NO:13:

( i ) SEQUENCE CHARACTERISTICS:
( A ) LENGTH: 40 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "synthetic DNA"

( x i ) SEQUENCE DESCRIPTION: SEQ ID NO:13:

TTAACATCGG CTTTGTCAGC TTCGCCCAGG GATTTCTCAT                40

( 2 ) INFORMATION FOR SEQ ID NO:14:

( i ) SEQUENCE CHARACTERISTICS:
( A ) LENGTH: 40 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "synthetic DNA"

( x i ) SEQUENCE DESCRIPTION: SEQ ID NO:14:

GAGATTCAAC CAGTACGTTA TCTTCTTTCT TACGCGGACG                40

( 2 ) INFORMATION FOR SEQ ID NO:15:

( i ) SEQUENCE CHARACTERISTICS:
( A ) LENGTH: 41 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "synthetic DNA"

( x i ) SEQUENCE DESCRIPTION: SEQ ID NO:15:

TTGGGATCCT GCATCACGTG GAGCCAGCGG TGCACCCAGC G              41

( 2 ) INFORMATION FOR SEQ ID NO:16:

( i ) SEQUENCE CHARACTERISTICS:
( A ) LENGTH: 41 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "synthetic DNA"

( x i ) SEQUENCE DESCRIPTION: SEQ ID NO:16:

CAACGAAGTT GTGGACGTCC TGCAGTTTCT TACGCAGCCA C              41

( 2 ) INFORMATION FOR SEQ ID NO:17:

( i ) SEQUENCE CHARACTERISTICS:
( A ) LENGTH: 41 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "synthetic DNA"

( x i ) SEQUENCE DESCRIPTION: SEQ ID NO:17:

TCGACGCGTT CCATGCTATT CAGGTGTTTG CCCAGGTTAT G              41

( 2 ) INFORMATION FOR SEQ ID NO:18:

( i ) SEQUENCE CHARACTERISTICS:
  ( A ) LENGTH: 46 base pairs
  ( B ) TYPE: nucleic acid
  ( C ) STRANDEDNESS: single
  ( D ) TOPOLOGY: linear ( i i ) MOLECULE TYPE: other nucleic acid
  ( A ) DESCRIPTION: /desc = "synthetic DNA"

( x i ) SEQUENCE DESCRIPTION: SEQ ID NO:18:

CATCAGCTGA ATTTCAGAAA CAGAACGCTT TTTAACAGAT TTCATG            46

( 2 ) INFORMATION FOR SEQ ID NO:19:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "synthetic DNA"

( x i ) SEQUENCE DESCRIPTION: SEQ ID NO:19:

TCGAGGTCGA CGGTACCGAG CTCG            24

( 2 ) INFORMATION FOR SEQ ID NO:20:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "synthetic DNA"

( x i ) SEQUENCE DESCRIPTION: SEQ ID NO:20:

AATTCGTGCT CGGTACCGTC GACC            24

( 2 ) INFORMATION FOR SEQ ID NO:21:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "synthetic DNA"

( x i ) SEQUENCE DESCRIPTION: SEQ ID NO:21:

AATTCGAGCT CGGTACCGTC GACC            24

( 2 ) INFORMATION FOR SEQ ID NO:22:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "synthetic DNA"

( x i ) SEQUENCE DESCRIPTION: SEQ ID NO:22:

TCGAGGTCGA CGGTACCGAG CTCG            24

( 2 ) INFORMATION FOR SEQ ID NO:23:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "synthetic DNA"

( x i ) SEQUENCE DESCRIPTION: SEQ ID NO:23:

TCGAGAAAGA AGAAGGCGTA AGCTTGGAAA AACGAT    36

( 2 ) INFORMATION FOR SEQ ID NO:24:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "synthetic DNA"

( x i ) SEQUENCE DESCRIPTION: SEQ ID NO:24:

CGTTTTTCCA AGCTTACGCC TTCTTCTTTC    30

( 2 ) INFORMATION FOR SEQ ID NO:25:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "synthetic DNA"

( x i ) SEQUENCE DESCRIPTION: SEQ ID NO:25:

GTTAAAAAGC GATCGGTTTC TGAAATTCAG CTG    33

( 2 ) INFORMATION FOR SEQ ID NO:26:

( i ) SEQUENCE CHARACTERISTICS:
    ( A ) LENGTH: 34 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "synthetic DNA"

( x i ) SEQUENCE DESCRIPTION: SEQ ID NO:26:

GCACCGGTAC CTTAGAAGTT GTGGACGTCC TGCA    34

( 2 ) INFORMATION FOR SEQ ID NO:27:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "synthetic DNA"

( x i ) SEQUENCE DESCRIPTION: SEQ ID NO:27:

GCTAAGGAAG AATTCATGGA GAAAAAAATC    30

( 2 ) INFORMATION FOR SEQ ID NO:28:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "synthetic DNA"

( x i ) SEQUENCE DESCRIPTION: SEQ ID NO:28:

CTGCCTTAAA ACTCGAGCGC CCCG    24

( 2 ) INFORMATION FOR SEQ ID NO:29:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "synthetic DNA"

( x i ) SEQUENCE DESCRIPTION: SEQ ID NO:29:

AAACTGCAGG ACGTCCACAA CTTCTAAGCG CTGGGTGCAC CGCGT    45

( 2 ) INFORMATION FOR SEQ ID NO:30:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "synthetic DNA"

( x i ) SEQUENCE DESCRIPTION: SEQ ID NO:30:

CATTAAAGCT TTGCGATGAT AAGC    24

( 2 ) INFORMATION FOR SEQ ID NO:31:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "synthetic DNA"

( x i ) SEQUENCE DESCRIPTION: SEQ ID NO:31:

CGCACCGATC GCCCTTCCCA ACAGTT    26

( 2 ) INFORMATION FOR SEQ ID NO:32:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "synthetic DNA"

( x i ) SEQUENCE DESCRIPTION: SEQ ID NO:32:

TTTCCCGGGC CTCCGTGGGA ACAAACGGCG GATTG    35

( 2 ) INFORMATION FOR SEQ ID NO:33:

( i ) SEQUENCE CHARACTERISTICS:
   ( A ) LENGTH: 42 base pairs
   ( B ) TYPE: nucleic acid
   ( C ) STRANDEDNESS: single
   ( D ) TOPOLOGY: linear ( i i ) MOLECULE TYPE: other nucleic acid
   ( A ) DESCRIPTION: /desc = "synthetic DNA"

( x i ) SEQUENCE DESCRIPTION: SEQ ID NO:33:

TTTCCCGGGA GGCCTTCTGT TAAAAAGCGG TCTGTTTCTG AA    42

( 2 ) INFORMATION FOR SEQ ID NO:34:

( i ) SEQUENCE CHARACTERISTICS:
      ( A ) LENGTH: 18 base pairs
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: /desc = "synthetic DNA"

( x i ) SEQUENCE DESCRIPTION: SEQ ID NO:34:

CACCATCATC ACCCTGGA    18

( 2 ) INFORMATION FOR SEQ ID NO:35:

( i ) SEQUENCE CHARACTERISTICS:
      ( A ) LENGTH: 18 base pairs
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: /desc = "synthetic DNA"

( x i ) SEQUENCE DESCRIPTION: SEQ ID NO:35:

TCCAGGGTGA TGATGGTG    18

( 2 ) INFORMATION FOR SEQ ID NO:36:

( i ) SEQUENCE CHARACTERISTICS:
      ( A ) LENGTH: 37 base pairs
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: /desc = "synthetic DNA"

( x i ) SEQUENCE DESCRIPTION: SEQ ID NO:36:

TAAGAATTCA TGAAAGTGAG GAAATATATT ACTTTAT    37

( 2 ) INFORMATION FOR SEQ ID NO:37:

( i ) SEQUENCE CHARACTERISTICS:
      ( A ) LENGTH: 35 base pairs
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: /desc = "synthetic DNA"

( x i ) SEQUENCE DESCRIPTION: SEQ ID NO:37:

TAAGTCGACT TAAGGATCGG TACTCGCAGT AGTCG    35

( 2 ) INFORMATION FOR SEQ ID NO:38:

( i ) SEQUENCE CHARACTERISTICS:
( A ) LENGTH: 35 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "synthetic DNA"

( x i ) SEQUENCE DESCRIPTION: SEQ ID NO:38:

TAAGTCGACT TAATAATGCA TGGCTTGCCT AGGAG 35

( 2 ) INFORMATION FOR SEQ ID NO:39:

( i ) SEQUENCE CHARACTERISTICS:
( A ) LENGTH: 39 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "synthetic DNA"

( x i ) SEQUENCE DESCRIPTION: SEQ ID NO:39:

TAAGTCGACT TAGGCGCCAA TCAAAATAT TGTTAAAAA 39

( 2 ) INFORMATION FOR SEQ ID NO:40:

( i ) SEQUENCE CHARACTERISTICS:
( A ) LENGTH: 39 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "synthetic DNA"

( x i ) SEQUENCE DESCRIPTION: SEQ ID NO:40:

TAAGTCGACT TACATAAAAA ACATGAAGTA TAACACCAA 39

( 2 ) INFORMATION FOR SEQ ID NO:41:

( i ) SEQUENCE CHARACTERISTICS:
( A ) LENGTH: 35 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "synthetic DNA"

( x i ) SEQUENCE DESCRIPTION: SEQ ID NO:41:

GCGGCCGCTT AAACATCCCG TTTTGTAAAA AGAGA 35

( 2 ) INFORMATION FOR SEQ ID NO:42:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "synthetic DNA"

( x i ) SEQUENCE DESCRIPTION: SEQ ID NO:42:

GGGGTCGACT TAAGAAGTTG AACTGGCAGA A 31

( 2 ) INFORMATION FOR SEQ ID NO:43:

(i) SEQUENCE CHARACTERISTICS:
    (A) LENGTH: 31 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "synthetic DNA"

(xi) SEQUENCE DESCRIPTION: SEQ ID NO:43:

GGGGTCGACT TAAGAAGATG TAGAAGTAGC G                           31

(2) INFORMATION FOR SEQ ID NO:44:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:44:

GGGGTCGACT TAAATGGCCG ACGTTTCCAC                              30

(2) INFORMATION FOR SEQ ID NO:45:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:45:

GGGGTCGACT TATGTTAAAA AATAATGCAT GGC                          33

PROCESS FOR PRODUCTION OF SECRETORY KEX2 DERIVATIVES

BACKGROUND OF INVENTION

1. Field of Invention

The present invention relates to Kex2 derivatives with Kex2 protease activity which are secreted in large amount in culture medium, and to a method for their production. The invention also relates to a method of using the aforementioned secretory Kex2 derivatives.

2. Related Art

Many attempts have been made at methods for producing physiologically active peptides by chimeric protein expression, and chemical or enzymatic cleavage methods have been used for release of the desired proteins. Chemical methods include cleavage of asparagine residue with nitrous acid and cleavage of methionine residue with CNBr (Itakura et al., Science 198, 1059, 1977). However, these methods necessarily involve modification of the protein of interest, and problems of purification cost.

Enzymatic methods employ lysyl endopeptidase which specifically cleaves the peptide bond of the C-terminal of lysine (Achromobacter protease I) and Staphylococcal protease V8 which specifically cleaves the peptide bond of the C-terminal of the glutamic acid (Japanese Examined Patent Publication No. 6-87788). However, since these chemical methods and endoproteases recognize a single amino acid residue, it is a precondition that amino acid residue not be present in the desired peptide in order to allow efficient excision of the desired peptide from the chimeric protein, and thus the peptides which can be produced are limited. Efforts have therefore been directed at developing a highly universal cleavage method which recognizes multiple amino acid residues.

Prohormone converting enzymes are enzymes which produce peptide hormones from their precursors in vivo, and they are expected to have favorable qualities as enzymes for excision of peptide hormones from proteins, even in vitro. Kex2 protease is a prohormone converting enzyme derived from *Saccharomyces cerevisiae*, and it is a calcium-dependent serine protease which specifically cleaves peptide bonds at the C-terminal ends of Lys-Arg, Arg-Arg and Pro-Arg sequences. Kex2 protease is a protein composed of 814 amino acid residues with a signal sequence at the N-terminus and a transmembrane region at the C-terminus with a continuous string of hydrophobic amino acids, and it is localized in the trans Golgi in cells.

A nucleotide sequence coding for Kex2 protease and the corresponding amino acid sequence are shown in the Sequence Listing as SEQ ID NO.1. Genetic expression of a Kex2 derivative lacking the C-terminal region in *Saccharomyces cerevisiae* and subsequent analysis thereof revealed that the Kex2 derivative with the amino acid sequence from amino acids 1 to 614 of SEQ ID NO.1 retains the Kex2 protease activity, and is secreted in culture medium (Fuller et al., Proc. Natl. Acad. Sci. USA, 86, 1434–1438, 1989, Japanese Unexamined Patent Publication No. 1-199578). In the present specification, the Kex2 protease derivative is represented by the number of amino acids counting from amino acid 1 of SEQ ID NO.1. For example, the Kex2 derivative with the amino acid sequence from amino acids 1 to 614 of SEQ ID NO.1 is represented as Kex2-614.

Heretofore known Kex2 derivatives whose secretory production methods have been studied include ss-Kex2 and Kex2Δp.

ss-Kex2 is a Kex2 derivative which has a 3 amino acid residue peptide added to Kex2-614, and its production in *Saccharomyces cerevisiae* has been studied (Brenner et al., Proc. Natl. Acad. Sci. USA, 89, 922–926, 1992). It was expressed in a protease-deficient mutant (pep4) as a host (in a 4 mg/L culture medium), and was purified from the culture supernatant at a purification yield of 20%. The reduced molecular weight of the purified ss-Kex2 treatment with Asn-type sugar chain hydrolyzing enzyme EndoH suggests that it includes Asn-type sugar chains. The pH dependency and substrate specificity of the enzyme activity has also been studied using synthetic substrates.

Kex2Δp is a Kex2 derivative represented in this specification by Kex2-666, and studies of its production in the insect cell host Sf9 have shown that 90% of its activity is secreted into the culture supernatant, and that the molecular weight of the secreted Kex2Δp is 70 kDa, which is smaller than the intracellular molecular weight of 120 kDa (Germain et al., Eur. J. Biochem. 204, 121–126, 1992). In addition, since the 70 kDa molecular weight protein is found in the culture supernatant in which Kex2 is expressed, and replacement of the 385th serine residue by alanine residue of Kex2Δp (the catalytic portion of Kex2 protease activity) results in Kex2Δp in the culture supernatant with a molecular weight of 120 kDa, equal to the intracellular molecular weight, the 70 kDa protein is believed to be an autolysate of the C-terminal portion-deficient Kex2Δp (120 kDa) in the culture medium.

Attempts have also been made at expression of the derivative Kex2Δ504 in which the cleavage site of the Lys-Arg sequence (amino acids 503-504 of SEQ ID NO.1), expected from the molecular weight of the decomposition product and the substrate specificity of Kex2 protease, is replaced with the Lys-Leu sequence. However in this case as well a 70 kDa protein is found in the culture medium, and since the Lys-Arg sequence is not always cleaved by Kex2Δp during autolysis, and no other sequence exists as the recognition site of Kex2 protease, this suggests the possibility that Kex2Δ504 recognizes a completely different sequence than the one predicted from the synthetic substrate, and cleaves itself.

Thus, despite research on substrate specificity of Kex2 derivatives using synthetic substrates, the substrate specificity when using proteins is not yet understood. Also, little is known about the secreted amounts of the different Kex2 derivatives, and it is still not known whether stable secretory production of Kex2 derivatives other than Kex2-614 is possible.

SUMMARY OF THE INVENTION

Here, the present inventors have completed the present invention with the purpose of providing a method for supplying a large amount of enzymes with Kex2 protease activity. The present invention also serves as experimental demonstration that the enzymes are useful for excision of desired peptides from chimeric proteins on an industrial scale.

Specifically, the use of enzymes with Kex2 protease activity for the production of useful peptides by chimeric protein expression on an industrial scale requires solution of the following three problems or objects.

The first object was an increase in the amount of production of the Kex2 derivatives. The enzyme having Kex2 protease activity with the greatest yield hitherto reported has been ss-Kex2, and that yield is about 4 mg per 1 L of culture medium. However, this yield is low in terms of production of enzyme for excision of desired peptides from chimeric proteins on an industrial scale. Also, since secretory Kex2 derivatives such as Kex2Δp are believed to possibly undergo autolysis in culture medium and the cleavage site cannot be predicted, it is unknown how to design derivatives to increase the yield.

Consequently, it is necessary to select Kex2 derivatives which do not undergo autolysis and to construct a high-expression system for those Kex2 derivatives. In the present specification, autolysis refers to decomposition which brings a reduction in Kex2 protease activity, and does not refer to maturation of Kex2 protease which accompanies the autocleavage of Lys-Arg (amino acids 108–109 of SEQ ID NO.1) (Brenner & Fuller, Proc. Natl. Acad. Sci. USA, 89, 922–926, 1992).

The second object was establishment of a purification process for high purity Kex2 derivatives without contamination by other proteases. The activity of Kex2 derivatives hitherto reported are evaluated using only synthetic substrates and not protein substrates, and thus the presence of contamination by other proteases cannot be determined. In particular, it is difficult to achieve precise control of reaction conditions when excising chimeric proteins on an industrial scale, and since contamination by other proteases can notably lower the recovery rates of the object peptides, the enzymes with Kex2 protease activity must be purified to a high degree.

The third object was setting the conditions for cleaving chimeric proteins by enzymes with Kex2 protease activity. It is well-known to those in the art that the tertiary structure of proteins affects enzyme activity, the enzyme stability under the reaction conditions and recognition of the substrate. However, almost no previous reports have dealt with these points. In particular, since chimeric proteins often form insoluble inclusion bodies in chimeric protein expression methods, denaturing agents such as urea are used for their solubilization. However, it is generally unknown what enzyme structure can retain enzyme activity in the presence of urea. Consequently, it is unclear whether or not Kex2 protease and secretory Kex2 derivatives can be used as enzymes for excision of desired peptides from proteins.

Mass production of other prohormone converting enzymes has also been unsuccessful, and it is also unknown whether these enzymes can be used as enzymes for excision of desired peptides from chimeric proteins in vitro. Consequently, in order to use prohormone converting enzymes, including Kex2 protease, as enzymes for releasing desired peptides from chimeric proteins, it is necessary to establish more efficient expression and purification methods, and set the cleavage conditions for using proteins as substrates in vitro.

As a result of research on methods of overcoming the problems described above, the present inventors have found that Kex2 derivatives having amino acid sequences from position 1 at the N-terminus to an amino acid at a position between 618 and 698 have notably higher secretory production without undergoing autolysis in culture, and that the production may be further increased by using methylotrophic yeast as the host cells, and have thus achieved mass supply of Kex2 derivatives. In addition, the inventors purified the secretory Kex2 derivatives from culture supernatant concentrates to single bands in SDS-PAGE by the 2 steps of anion exchange chromatography and hydrophobic chromatography, and have confirmed that, under conditions in which desired peptides are excised from chimeric proteins, the purified Kex2 derivatives contain no other protease activity which decomposes the peptides and lowers the recovery rate.

Furthermore, it was found that under conditions in which desired peptides are excised from chimeric proteins, the substrate specificity of secretory Kex2 derivatives is altered by changing urea concentration, and have demonstrated that a desired peptide can be excised from a chimeric protein at an efficiency of 75% even when the desired peptide includes 2 recognition sites for Kex2 protease. It was also demonstrated that Kex2-660 can be used to excise hPTH (1-34) from the chimeric protein βGal-117S4HPPH34 on a semi-large scale, i.e. that for the secretory Kex2 derivative, the yield, purity and excision efficiency of the desired peptide from the chimeric protein can be suitable for production on an industrial scale, and the present invention has thus been completed.

In order to solve the problems or objects described above, the present invention provides proteins with Kex2 protease activity which are obtained by transforming host cells with an expression vector comprising DNA coding for a natural amino acid sequence whose N-terminus is the Met at amino acid 1 and whose C-terminus is one of the amino acids between amino acids 618 and 698 of the amino acid sequence of the Kex2 protease represented by SEQ ID NO.1, or an amino acid sequence which is this natural amino acid sequence modified by a substitution, deletion or addition of one or more amino acids, and then culturing the resulting transformants and recovering the protein from the culture. In the specification, such proteins are collectively referred to as "enzymes with Kex2 protease activity", "Kex2 protease derivatives", "secretory Kex2 derivatives", etc.

The present invention further provides genes, particularly DNA, coding for the aforementioned proteins, vectors, particularly expression vectors, comprising the aforementioned DNA, and transformants, preferably animal cells or yeast, obtained by transforming host cells with the aforementioned vector.

The present invention still further provides a method for producing the aforementioned proteins, comprising the steps of culturing a host which has been transformed with the aforementioned expression vector and recovering the aforementioned protein from the culture. The protein is preferably recovered from the culture supernatant by anion exchange chromatography and hydrophobic chromatography.

The present invention still further provides a method for excision of desired peptides from chimeric proteins using the aforementioned proteins. Chimeric protein is a protein obtained by adding a protective peptide to a desired peptide, and the desired peptide may be excised by the aforementioned protein so long as the link between the desired peptide and the protective peptide is an amino acid sequence recognized by the aforementioned protein. Also, even if the junction between a desired peptide and a protective peptide is not an amino acid sequence recognized by the aforementioned protein, a recognition site of the aforementioned protein may be inserted between the desired peptide and the protective peptide to allow the desired peptide to be excised using the aforementioned protein.

BRIEF DESCRIPTION OF THE DRAWINGS

FIG. 1 shows the sequences of a synthetic oligomers used for construction of a synthetic hProPTH (1-84) gene.

FIG. 2 shows a process for constructing the synthetic hProPTH (1-84) gene.

FIG. 4 shows a process for constructing plasmid pGP#19 which expresses the chimeric protein βGal-139S(FM)PPH84.

FIG. 21 shows an elution profile of HPLC for before and after Kex2-660 processing of the chimeric protein CATPH34.

DETAILED DESCRIPTION

Figure 3:
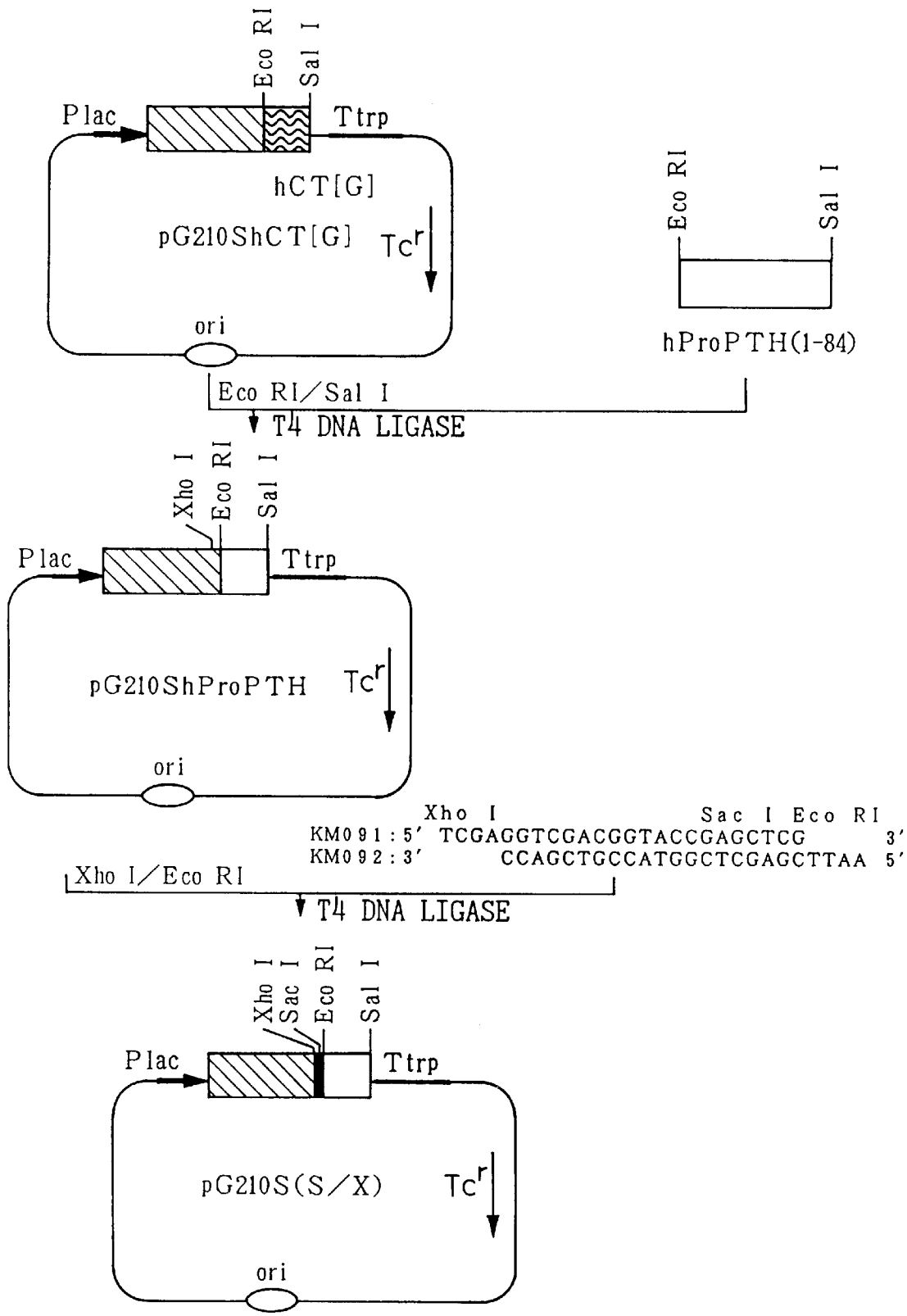
FIG. 3 shows a process for constructing plasmid pG210S (S/X). Plac represents the *E. coli* lactose operon promoter and Ttrp represents the *E. coli* TrpE attenuator terminator.

As will be explained hereunder, the proteins according to the present invention differ considerably in terms of production and secretion efficiency depending on the length of the protein and particularly the position on the C-terminus. The invention provides proteins of lengths which give high production and secretion efficiency, and the Kex2 derivatives have amino acid sequences from Met at amino acid 1 to any of the amino acids at positions 618 to 698 of the amino acid sequence represented by SEQ ID NO.1. The C-terminus of a Kex2 protease derivative of the present invention is preferably any one of the amino acids from the position 630 to the position 688 of the amino acid sequence of SEQ ID NO.1, more preferably it is any one of the amino acids from the position 360 to the position 682 of the amino acid sequence of SEQ ID NO. 2 and more preferably it is any one of the amino acids from the position 630 to the position 679. The above-mentioned amino acid sequences composed of portions of the amino acid sequence of SEQ ID NO.1 are sometimes referred to as natural amino acid sequences for the purpose of the present invention.

However, it is well-known among those in the art that enzyme activity can be maintained even with substitutions of multiple amino acids by other amino acids, deletion of amino acids or addition of amino acids in regions of amino acid sequences of an enzyme protein other than those regions participating in their activity. Therefore, the present invention also encompasses, in addition to Kex2 protease derivatives having the aforementioned natural amino acid sequences, also proteins with Kex2 protease activity having amino acid sequences which are the aforementioned natural amino acid sequences modified by a substitution, deletion or addition of one or more amino acids.

The present invention still further provides genes, particularly DNA, coding for the aforementioned various polypeptides. The DNA may be prepared according to a conventional method, for example from full-length DNA having the nucleotide sequence represented by SEQ ID NO.1 or another nucleotide sequence coding for the same amino acid sequence, or by cleaving a DNA containing the object DNA, and linking the cleavage product to an oligonucleotide if desired or by introducing a translation termination codon at a suitable location in the DNA. Alternatively, DNA coding for one of the aforementioned modified amino acid sequences may be prepared by a conventional method such as site-directed mutagenesis or the polymerase chain reaction (PCR), using the natural full-length DNA having the nucleotide sequence represented by SEQ ID NO.1 or a fragment thereof as a template, and using a primer oligonucleotide containing a desired mutation as a mutagenic primer.

The expression vector according to the invention contains an expression regulating region such as a promoter which is functional in the host used. For example, when yeast cells are used as the host, glyceraldehyde-3-phosphate dehydrogenase promoter, glycerophosphate kinase promoter, acid phosphatase promoter, alcohol oxidase promoter, formate dehydrogenase promoter, methanol oxidase promoter or the like may be used.

The host cells used according to the invention may be yeast cells. The yeast cells are preferably from Saccharomyces, Pichia, Hansenula or Candida, which include *Saccharomyces cerevisiae, Pichia pastoris, Hansenula polymorpha* and *Candida boidinii*. Especially preferred yeast is methylotrophic yeast, such as the genera Candida and Pichia, such as *Candida beidinii* and *Pichia pastoris*.

In order to render enzymes with Kex2 protease activity usable as enzymes for excision of peptides from chimeric proteins on an industrial scale, the present inventors determined that it was necessary to solve the problems of 1) providing high yields for large supply, 2) high purity, without contamination with other proteases cleaving the desired peptide and 3) establishing conditions for cleavage of substrate protein, and to this end the inventors carried out the following investigation.

First, we studied the conditions for increasing the yield of enzymes with Kex2 protease activity to deal with the first object. For the purification on an industrial scale of a large amount of enzymes with Kex2 protease activity, not only must the yield be high, but the purification thereof must also be simple, and for this purpose the inventors considered it advantageous to secrete the Kex2 derivatives in culture medium containing few other proteins. The secretory Kex2 derivative ssKex2 has been reported as mentioned above, but its yield is 4 mg/L culture medium which is too low for use on an industrial scale. Thus, genes coding for different secretory Kex2 derivatives were prepared and expressed in *Saccharomyces cerevisiae* hosts to examine the secretion yields.

The Kex2 derivatives used for the invention are Kex2-614, Kex2-630, Kex2-640, Kex2-650, Kex2-660, Kex2-679, Kex2-682, Kex2-688 and Kex2-699. For the expression of Kex2 derivative genes, the *Saccharomyces cerevisiae* glyceraldehyde-3-phosphate dehydrogenase (GAP) gene promoter was used. Plasmids containing these expression units were introduced into *Saccharomyces cerevisiae*, which was then cultured overnight at 30° C., and the Xex2 protease activities in the cultures were measured using the synthetic substrate Boc-Leu-Arg-Arg-MCA as the substrate.

As a result, Kex2 protease activity was detected in the culture supernatants of the yeast in which expression units of genes for Kex2-614, Kex2-630, Kex2-640, Kex2-650, Kex2-660, Kex2-679, Kex2-682 or Kex2-688 had been introduced, but no activity was detected in the culture supernatant of the yeast in which the expression unit of the Kex2-699 gene had been introduced. This demonstrated that secretion of Kex2 derivatives in culture supernatants can be achieved using derivative genes including amino acid residues from position 1 to position m (m=614 to 688) from the N-terminus.

Furthermore, the secretion yields per OD660 were found in Example 1 to be significantly higher for Kex2-660 and Kex2-679 than for the hitherto reported Kex2-614. Also, the results from analysis of SDS-PAGE of samples prepared to 20-fold concentration by ultrafiltration membrane of 10,000 molecular weight fraction of the culture supernatants showed that not only the Kex2 activity but also the amounts of secretion of Kex2-660 and Kex2-679 were greater than Kex2-614. It was demonstrated that the molecular weights increased with greater numbers of amino acid residues, i.e. no autolysis accumulated in this culturing as occurred with Kex2Δp in the insect cell host Sf9.

Furthermore, in Example 9 it was shown that the OD660 Kex2 activities of cultures of Kex2-630, Kex2-640, Kex2-650, Kex2-660 and Kex2-679 were at least 10 times higher than the hitherto reported Kex2-614, and the Kex2 activities of Kex2-682 and Kex2-688 were 6 times and 3.4 times greater, respectively, than Kex2-614, while the Kex2 activity of Kex2-699 was undetectable.

In other words, it was shown that the Kex2 activity of the culture increases when the C-terminal amino acid residues of the expressed Kex2 derivative are up to the 630-679th amino acid residues of Kex2, while the activity decreases as the C-terminal region extends beyond that length.

Also, the results of SDS-PAGE analysis confirmed that the amount of Kex2 secretion had increased. It was also demonstrated that the molecular weights increase with more amino acid residues of the Kex2 derivatives, and thus no autolysates accumulated in this culturing as occurred with Kex2Δp production in the insect cell host Sf9.

Since the secretory Kex2 derivatives prepared here were found to accumulate in the culture supernatants without undergoing autolysis, the Kex2-660 production test was conducted changing the expression system from the *Saccharomyces cerevisiae* system to for example an expression system with the methylotrophic yeast *Candida boidinii* as the host, which has a high production yield per culture. As a result, it was possible to increase the yield to 340 mg per 1 L of culture supernatant. This is the amount capable of releasing about 200 g of the physiologically active peptide hPTH(1-34) from a chimeric protein, and thus it was demonstrated that the present invention is able to supply an amount of enzyme necessary for excision of useful peptides from chimeric proteins on an industrial scale. In addition, it was found that yeast of the genus Candida is especially preferable as host.

The second problem to be dealt with was the purity of the secretory Kex2 derivatives. First, Kex2-660 which had the largest secretion yield was purified from the culture supernatant. Kex2-660 secreted extracellularly by *Saccharomyces cerevisiae* was purified to a single band (57% yield) by concentrating the culture supernatant with ultrafiltration (molecular weight 30,000) in the presence of 0.2 mM calcium, and subjecting it to anion exchange chromatography and hydrophobic chromatography. This recovery rate was the highest yet reported, thus demonstrating that this method allows high purity Kex2 derivatives to be supplied in large amounts.

Also, in order to determine the substrate specificity of the Kex2 derivatives using protein substrates, as well as the possibility of contamination with other proteases, an excess of purified Kex2-660 was allowed to act on the chimeric protein βGal-139S(FM)PPH84, and the structures of the resulting peptides were determined. βGal-139S(FM)PPH84 is a chimeric protein prepared by linking hPTH(1-84) via a Phe-Met sequence and a human parathyroid hormone-derived prosequence (Lys-Ser-Val-Lys-Lys-Arg) to βGal-139S, which is a polypeptide from the N-terminus to the 139rd amino acid residue of *E. coli* β-galactosidase which has been substituted with serine residues at its 76th and 122nd cysteine residues. The amino acid sequence of βGal-139S is represented as SEQ ID NO.2, and the amino acid sequence of hPTH(1-84) is represented as SEQ ID NO.3.

As a result, it was found that the sequence at the N-terminus of the resulting peptide is derived from the peptide fragment expected from the substrate specificity of Kex2 protease, and that the purified Kex2-660 had no contamination by other proteases which might interfere with excision of the desired peptide from the chimeric protein.

The purified Kex2-660 was used to investigate the cleavage conditions when using a protein as the substrate, in order to deal with the third object.

First, we studied the effect of urea, which is commonly used for releasing desired peptides from chimeric proteins. Kex2-660 was allowed to act on the synthetic substrate Boc-Leu-Arg-Arg-MCA in the presence of 0 to 4.0M urea, and it was found that at concentrations of 1.0M, 2.0M and 4.0M the activities were reduced to 70%, 40% and 10%, respectively, compared to absence of urea. When insoluble inclusion bodies are dissolved in a urea solution and protease acts thereon, the concentration of the urea solution is generally 2.0 to 4.0M. Thus, it was concluded that Kex2-660 can be used for excision of desired peptides from chimeric proteins, if the dissolution conditions of the chimeric proteins are appropriately determined.

Next, the effect of 1.5 to 3.0M urea on action of Kex2-660 on the chimeric protein βGal-139S(FM)PPH84 was investigated. The sequences predicted to be cleaved by Kex2 protease are at the 4 sites of Arg-Arg (amino acids 13–14 of SEQ ID NO.2, hereunder referred to as cleavage site A), Lys-Arg (prosequence portion, hereunder referred to as cleavage site B) and Pro-Arg (amino acids 43–44 and 51–52 of SEQ ID NO.3, hereunder referred to as cleavage sites C and D, respectively). The C-terminal ends of each of the sites are cleaved by the protease.

As a result of investigating the structures and amounts of the peptide fragments produced by the Kex2 protease processing, it was found that higher urea concentrations in the range of 1.5 to 2.5M gave higher cleavage efficiency by Kex2-660, while there was no difference in cleavage efficiency at urea concentrations of 2.5M and 3.0M. In addition, with regard to the effect of urea on substrate specificity, it was found that the cleavage efficiency at cleavage site B improved as the urea concentration increased, but the cleavage efficiency at cleavage site C reached a peak at 2.5M urea concentration, and thus higher urea concentrations gave better yields of hPTH(1-84) from the chimeric proteins. Also, no cleavage was found at cleavage site D. The same tendency was observed even at urea concentrations of 3.0 to 4.0M. These discoveries were unpredictable from using synthetic substrates, and were first arrived at by the present invention.

Figure 20:
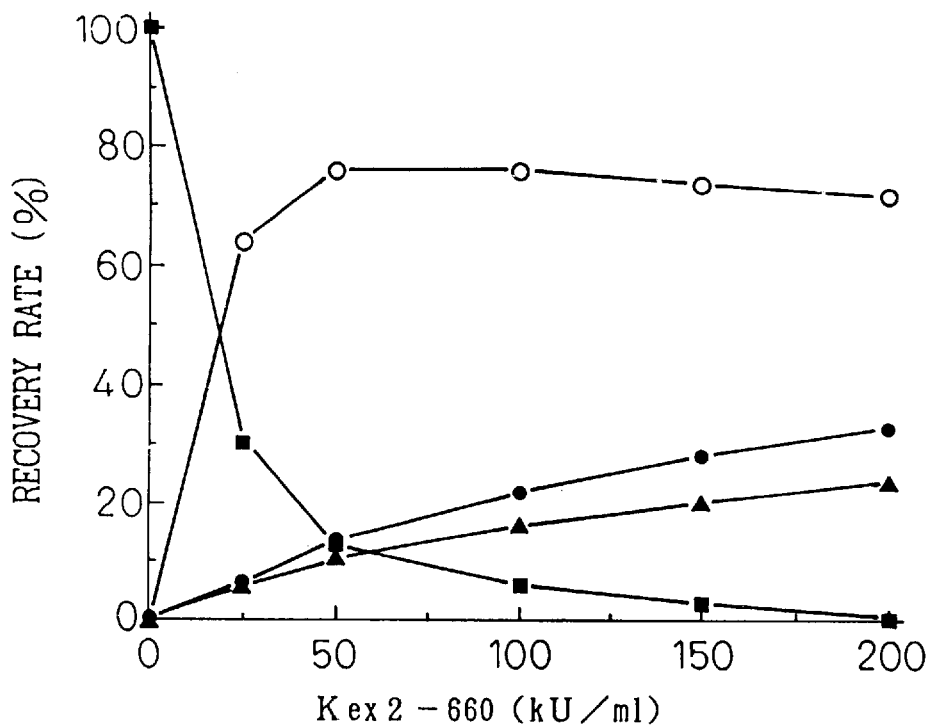
FIG. 20 is a graph comparing the recovery rates of hPTH(1-84), hPTH(1-44) and hPTH(45-84) from βGal-139S(FM)PPH84, at different enzyme concentrations. The solid squares, open circles, solid circles and solid triangles represent, respectively, recovery rates for βGal-139S(FM)PPH84, hPTH(1-84), hPTH(1-44) and hPTH(45-84). The recovery rates were calculated in the following manner. For hPTH(1-84) and βGal-139S(FM)PPH84, the peak area ratio against a known concentration of a corresponding standard substance was used, and for hPTH(1-44) and hPTH(45-84) the peak area ratio against a known concentration of hPTH (1-84) was used, and compensation was made based on the number of amino acid residues of the corresponding peptides.

The inventors then studied the conditions for excision of hPTH(1-84) from βGal-139S(FM)PPH84 using Kex2-660. Kex2-660 was used at different proportions (25 kU, 50 kU, 100 kU, 150 kU and 200 kU of Kex2-660 to 1 mg of chimeric protein) under conditions at which hPTH(1-84) is excised from chimeric proteins, and the structures of the resulting peptide fragments and their yields were examined. When 50 kU/ml of Kex2-660 was used, hPTH(1-84) was excised at an efficiency of about 75%. Here, about 10% of the βGal-139S(FM)PPH84 remained.

βGal-139S(FM)PPH84 decreased with increasing amounts of Kex2-660, and almost completely disappeared at 200 kU/ml. However, it was also found that the proportion of hPTH(1-44) and hPTH(45-84) also increased simultaneously, while the efficiency of hPTH(1-84) underwent no increase (FIG. 20). On the other hand, no decrease in the amount of hPTH(1-84) was seen beyond the increase in hPTH(1-44) even with increasing amounts of Kex2-660, and thus it was confirmed that the Kex2-660 purified in Example 2 described hereunder had no contamination by other proteases with different substrate specificities than Kex2 protease under conditions at which hPTH(1-84) is excised from chimeric proteins.

Furthermore, it was demonstrated that selection of the reaction conditions allows desired peptides to be efficiently excised (with an excision of efficiency of 75%) from chimeric proteins even when the desired peptide includes a cleavage site for the Kex2 protease. This excision of efficiency is higher than the excision of efficiency of 50% for hPTH(1-84) using factor-Xa (Gardella et al., J. Biol. Chem. 265, 26, 15854-15859, 1990).

Gardella et al. suggested the possibility that contaminating proteases or factor-Xa itself degrades hPTH(1-84), judging from lower hPTH(1-84) recovery rates when the enzyme amount is increased or the reaction time is extended, despite the fact that hPTH(1-84) does not include the factor-Xa recognition site, i.e. the Ile-Glu-Gly-Arg sequence. The fact that hPTH(1-84) is obtained at a high recovery rate despite the fact that hPTH(1-84) includes 2 sites of cleavage sequences for Kex2 protease suggests that the purified Kex2 derivatives with increased yields according to the invention are useful as enzymes for excision of desired peptides from chimeric proteins.

Furthermore, it was found that the purified Kex2-660 can excise hPTH(1-34) from the soluble chimeric protein CATPH34 in the absence of urea and from the insoluble chimeric protein βGal-117S4HPPH34 in the presence of urea, and thus it functions even when the substrates are chimeric proteins with different protective peptides and cleavage site regions, showing that it has wide industrial application. Also, no protease contamination was detected even in the absence of urea.

In other words, it was found that secretory Kex2 derivatives with increased yields which are purified to a single band degrade desired peptides under conditions in which the desired peptides are released from chimeric proteins, irrespective of the presence or absence of urea, and have no contamination of other proteases which lower the recovery rates, that selection of the conditions allows these Kex2 derivatives to recover the desired peptides very efficiently even when the desired peptides include recognition sites for the Kex2 proteases, and that the amounts of expression per 1 L of culture medium are sufficient for release of about 200 g of the desired peptides and thus the secretory Kex2 derivatives obtained according to the invention are supplied in amounts necessary for excision of desired peptides from chimeric proteins on an industrial scale.

EXAMPLES

The present invention will now be explained in more detail by way of the following Reference Examples and Examples which, however, are not intended to restrict the invention. The plasmids, $E.$ $coli$ and yeast used as materials for the invention and the basic experimental procedures employed for all of the examples will be described first, and then the Reference Examples and Examples will be presented.

Plasmids

Plasmid pG97S4DhCT[G] is a plasmid which is capable of expressing a chimeric protein wherein hCT[G] (a peptide resulting from addition of a glycine residue to the C-terminus of the 32nd amino acid of human calcitonin) has been linked to a peptide comprising the region from the N-terminus to the 97th amino acid of β-galactosidase (where the 76th cysteine residue is replaced by a serine residue and the 40th, 41st, 71st and 75th glutamic acid residues are replaced by aspartic acid residues: named βGal-97S4D) via a glutamic acid residue, under the $E.$ $coli$ lactose operon promoter.

By introducing a DNA region coding for the desired peptide in reading frame as an EcoRI-SalI DNA fragment, it is possible to express a chimeric protein with βGal-97S4D. The $E.$ $coli$ strain W3110 containing this plasmid was named $Escherichia$ $coli$ SBM323, and was deposited at the National Institute of Bioscience and Human Technology on Aug. 8, 1991 as FERM BP-3503.

Plasmid ptacCAT is a plasmid which is capable of expressing the chloramphenicol acetyltransferase gene under the synthetic promoter tac. The $E.$ $coli$ strain JM1O9 containing this plasmid was named $Escherichia$ $coli$ SBM336, and was deposited at the National Institute of Bioscience and Human Technology on Mar. 1, 1996 as FERM BP-5436. pG97S4DhCT[G] and ptacCAT were used as materials to construct the soluble hPTH(1-34) chimeric protein-expressing vector ptacCATPTH(1-34) (Reference Example 2 and FIGS. 5 and 6).

Plasmid pG210ShCT[G] is a plasmid in which the gene coding for βGal-97S4D from pG97S4DhCT[G] is replaced with the gene coding for βGal-210S (a peptide consisting of the N-terminus to the 210th amino acid of β-galactosidase, wherein the 76th, 122nd and 154th cysteine residues are replaced with serine residues).

Figure 24:
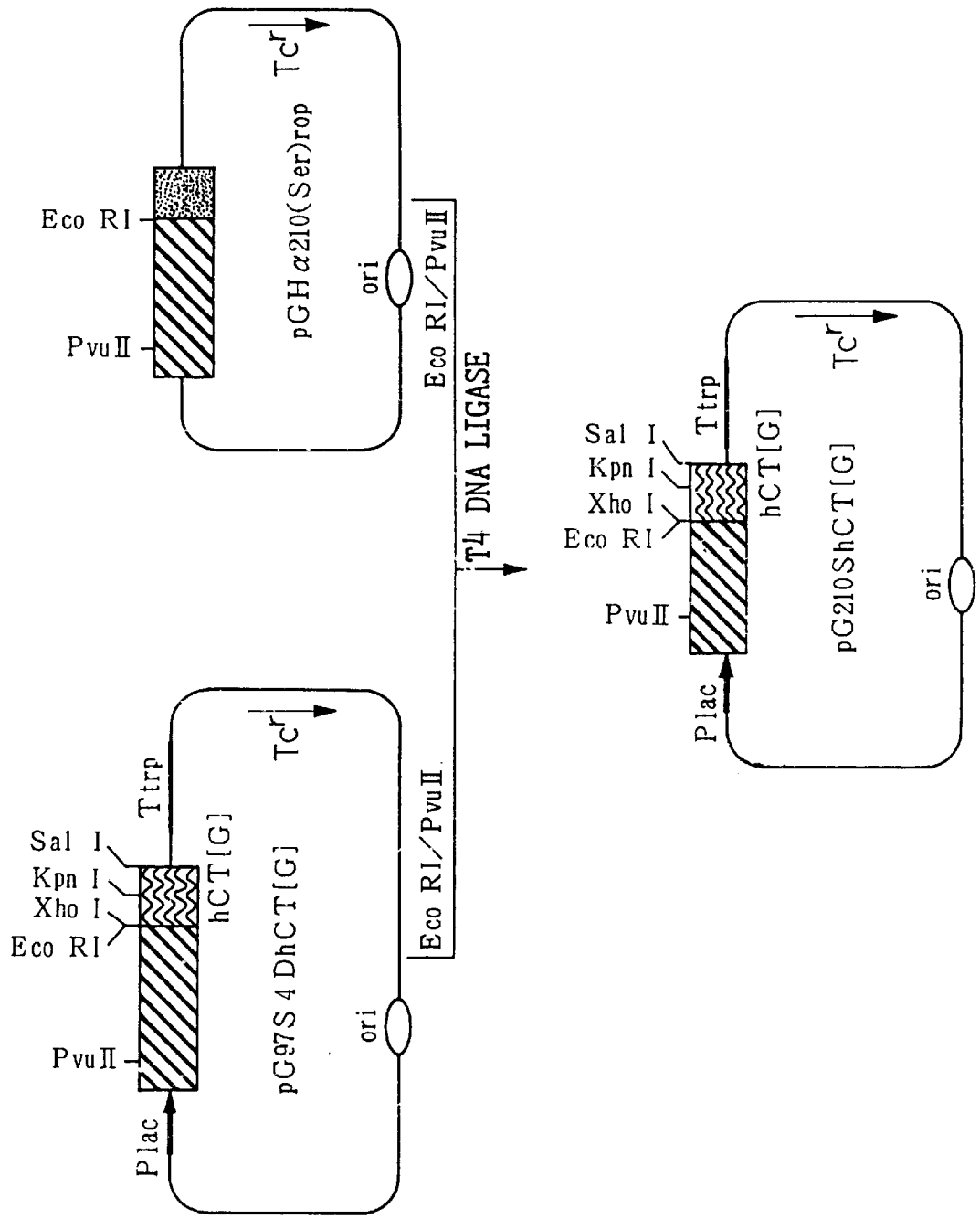
FIG. 24 shows a process for constructing plasmid pG210ShCT[G].

Plasmid PG21OShCT[G] can be obtained by linking of a DNA fragment containing the gene coding for βGal-210S obtained by digesting pGHα210(Ser)rop⁻ with restriction enzymes PvuII and EcoRI and a DNA fragment containing a vector portion obtained by digesting pG97S4DhCT[G] with restriction enzymes PvuII and EcoRI (FIG. 24). A method for constructing pGHα210(Ser)rop⁻ is disclosed in Japanese Examined Patent Publication No. 6-87788. pG210ShCT[G] was used as material for cloning of a synthetic human parathyroid hormone precursor (hProPTH (1-84)) gene and construction of plasmid pGP#19 (Reference Example 1 and FIG. 5).

Plasmid PCRII was acquired from Invitrogen Co. and used for direct cloning of the PCR products.

Figure 12:
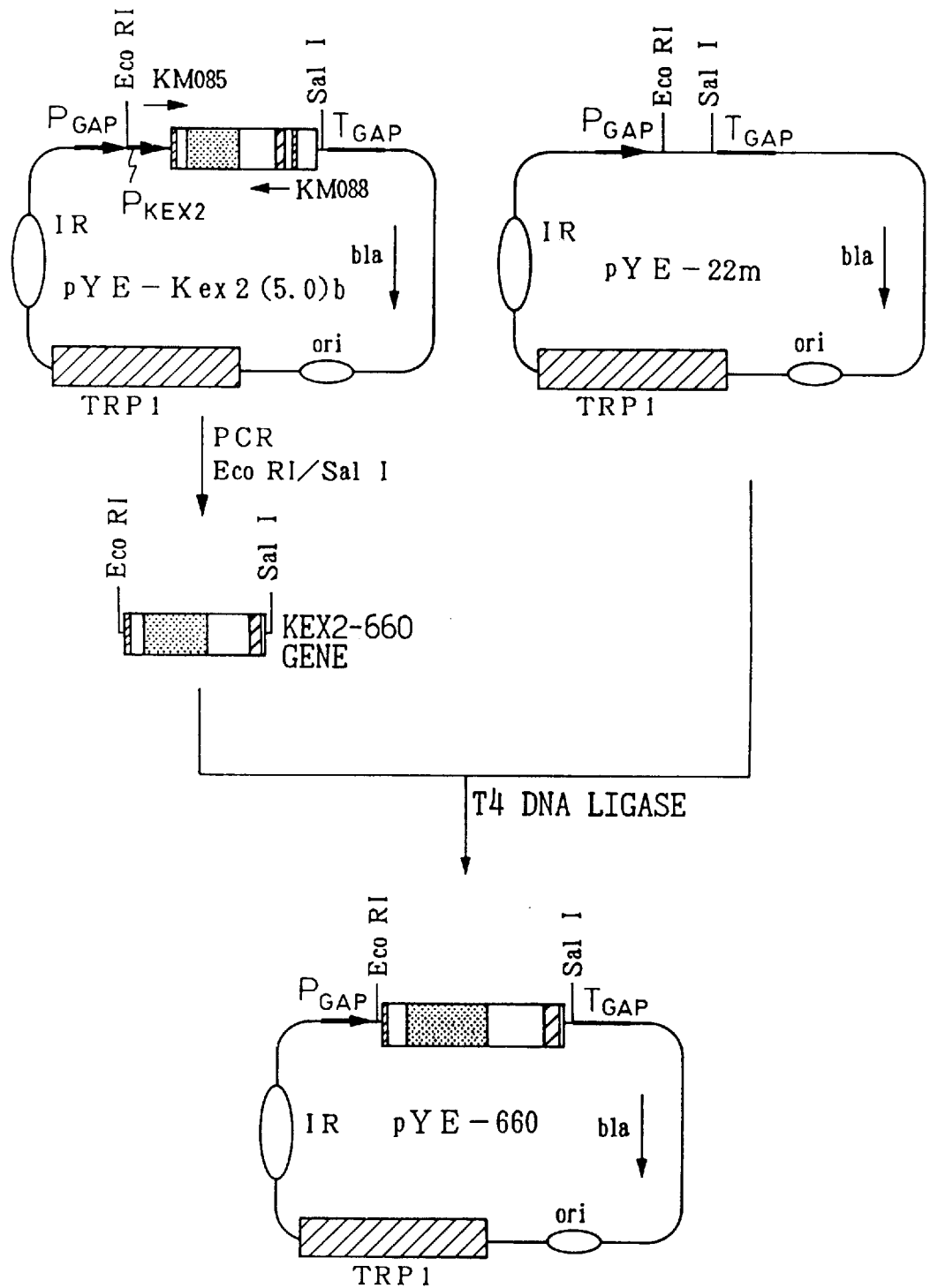
FIG. 12 shows a process for constructing plasmid pYE-660 which expresses a secretory Kex2 derivative. PKEX2 represents a promoter for the KEX2 gene of *Saccharomyces cerevisiae*.

Plasmid pYE-22m is an expression vector which utilizes the promoter and terminator for the glyceraldehyde-3-phosphate dehydrogenase (GAP) gene and has a multicloning site (MCS: EcoRI→SalI), with the promoter at the EcoRI end, the TRP1 gene as the selective marker, and a 2 μm DNA portion (inverted repeats) at the replication origin. The $E.$ $coli$ strain JM109 containing plasmid pYE-22m was named Escherichia coli SBM335, and was deposited at the National Institute of Bioscience and Human Technology on Mar. 1, 1996 as FERM BP-5435 (FIG. 12).

Figure 13:
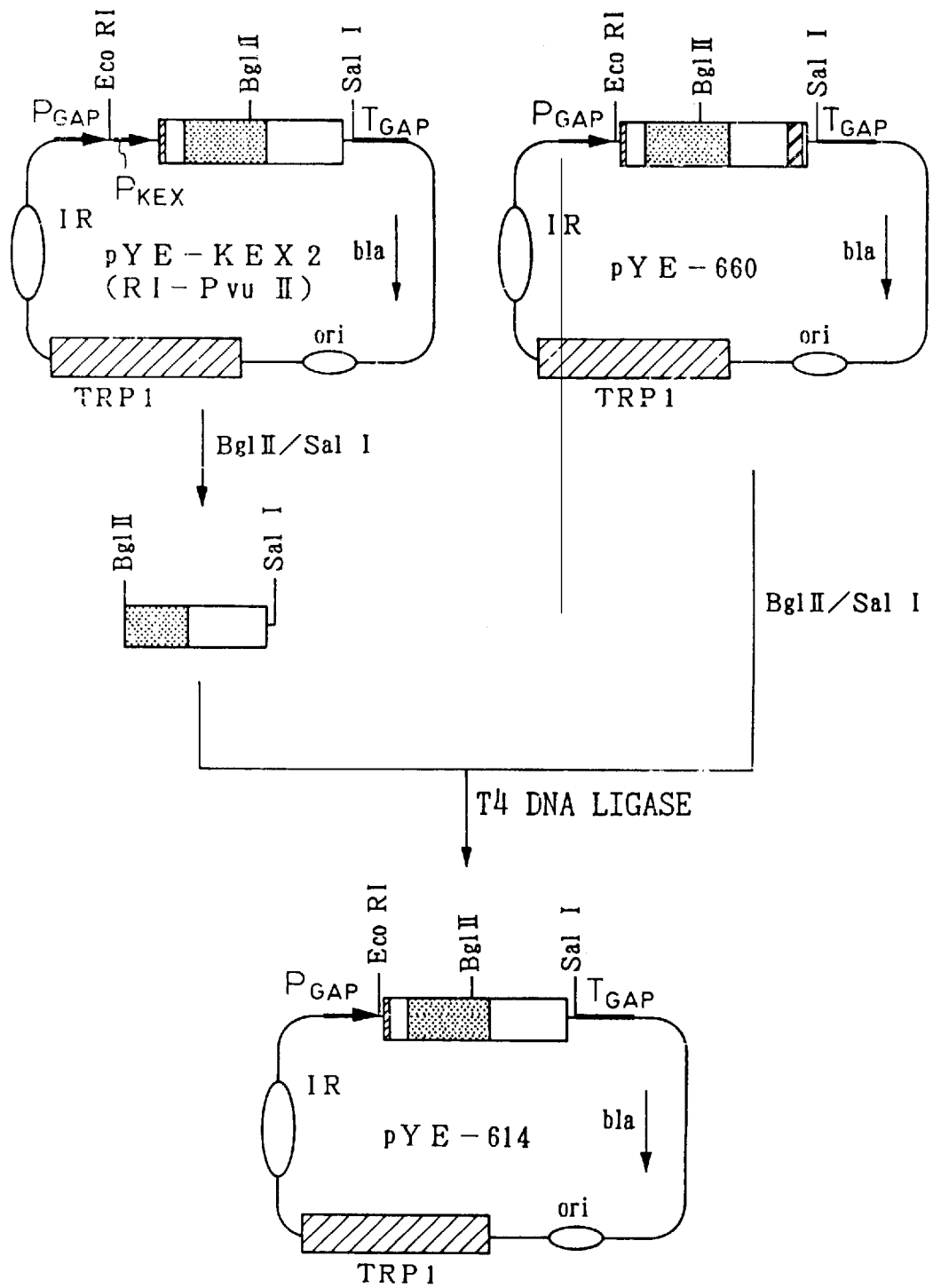
FIG. 13 shows a process for constructing plasmid pYE-614 which expresses Kex2-614.

Plasmid pYE-KEX2 (5.0)b (Mizuno et al., Biochem. Biophys. Res. Commun. 156, 246–254, 1988) was used as a template to construct Kex2 derivative genes by the PCR (FIG. 12). Plasmid pYE-KEX2 (RI-PvuII) (Japanese Unexamined Patent Publication No. 1-199578) was used to construct the expression vector pYE-614 for a protein comprising a peptide of 14 amino acids (SEQ ID NO.4) at the C-terminus of Kex2-614 (FIG. 13).

Plasmid pNOTe1I is an expression vector which utilizes the promoter and terminator for the alcohol oxidase gene and which includes a restriction enzyme NotI site, with the URA3 gene as the selective marker (Japanese Unexamined Patent Publication No. 5-344895).

E. coli and yeast

The competent cell line $E.$ $coli$ JM109 was acquired from Toyobo and used for plasmid preparation and chimeric protein expression. $E.$ $coli$ JM101 and M25 (Sugimura et al., Biochem. Biophys. Res. Commun. 153, 753–759, 1988) were used for production of the chimeric proteins CATPH34 and βGal-117S4HPPH34, respectively. The hosts used for secretory expression of the Kex2 proteases were Saccharomyces cerevisiae K16-57C (MAT α leu2 trp1 ura3 kex2-8: Mizuno et al., Biochem. Biophys. Res. Commun. 156, 246–254, 1988) and $Candida$ $boidinii$ TK62.

TK62 is a uracil-requiring cell line obtained by URA3 mutation from $Candida$ $boidinii$ S2AOU-1 (Sakai, Y. et al., J. Bacteriol., 173, 7458–7463, 1991). This $Candida$ $boidinii$ S2AOU-1 strain was named $Candida$ $boidinii$ SAM1958, and was deposited at the National Institute of Bioscience and Human Technology on Feb. 25, 1992 as FERM BP-3766.

Culture media

For culturing of $E.$ $coli$, an LB medium (0.5% (w/v) yeast extract, 1% (w/v) tryptone, 0.5% (w/v) NaCl), SB medium (1.2% (w/v) yeast extract, 2.4% (w/v) tryptone, 0.5% (v/v) glycerol), SB2 medium (2% (w/v) yeast extract, 1% (w/v) tryptone, 0.5% (v/v) glycerol, 1.2% (w/v) $K_2HPO_4$, 0.3% (w/v) $KH_2PO_4$) and NU medium (0.3% (w/v) yeast extract, 1.5% (w/v) glucose, 0.3% (w/v) $KH_2PO_4$, 0.3% (w/v) $K_2HPO_4$, 0.27% (w/v) $Na_2HPO_4$, 0.12% (w/v) $(NH_4)_2SO_4$, 0.2 g/L $NH_4Cl$, 0.2% (w/v) $MgSO_4$, 40 mg/L $FeSO_4.7H_2O$, 40 mg/L $CaCl_2.2H_2O$, 10 mg/L $MnSO_4.nH_2O$, 10 mg/L $AlCl_3.6H_2O$, 4 mg/L $CoCl_2.6H_2O$, 2 mg/L $ZnSO_4.7H_2O$, 2 mg/L $Na_2MoO_4.2H_2O$, 1 mg/L $CuCl_2.7H_2O$, 0.5 mg/L $H_3BO_3$) were used.

For culturing of $Saccharomyces$ $cerevisiae$, YCDP medium (1% (w/v) yeast extract, 2% (w/v) casamino acid, 2% (w/v) glucose, 100 mM potassium phosphate (pH 6.0)) was used.

For culturing of $Candida$ $boidinii$ and $Pichia$ $pastoris$, BMGY medium (1% (w/v) yeast extract, 2% (w/v) peptone, 1% (v/v) glycerol, 1.34% (v/v) YNB w/o AA: Yeast Nitrogen Base without Amino Acids, 0.4 mg/L biotin, 100 mM potassium phosphate (pH 6.0)), BMMY medium (1% (w/v) yeast extract, 2% (w/v) peptone, 0.5% (v/v) methanol, 1.34% (v/v) YNB w/o AA, 0.4 mg/L biotin, 100 mM potassium phosphate (pH6.0)), YPD medium (1% (w/v) yeast extract, 2% (w/v) peptone, 2% (w/v) glucose) and YPGM medium (1% (w/v) yeast extract, 2% (w/v) peptone, 3% (v/v) glycerol, 1% (v/v) methanol, 1.34% (v/v) YNB w/o AA, 50 mM potassium phosphate (pH6.0)) were used.

Basic experimental procedure

Unless otherwise specified, the experimental procedures in the Reference Examples and Examples were according to the following methods.

The DNA primers were synthesized by the phosphoramidite method using an automatic synthesizer (Model 380A, Applied Biosystems). The DNA nucleotide sequences were determined by the dideoxy method.

Cleavage of the DNA with restriction enzymes was accomplished by reaction for one hour using 3- to 10-fold amounts of the enzyme as indicated by the manufacturer. Analysis of the plasmid structures was made using 0.5 to 1 µg of DNA in a 20 µl reaction solution, and the DNA was prepared using 3 to 10 µg of DNA in a 50 to 100 µl reaction solution. The reaction temperature and reaction buffer conditions were as indicated by the manufacturer.

Agarose gel electrophoresis samples were prepared by adding a ⅕ volume of a pigment solution (15% (w/v) Ficoll aqueous solution containing 0.25% (w/v) bromphenol blue) to the reaction solution. The agarose gel electrophoresis buffer used was a TAE buffer (10 mM Tris, 20 mM acetic acid, 2 mM EDTA). For structural analysis of the plasmids, Mupid-2 (Cosmo Bio, KK.) was used for electrophoresis at 100 volts for one hour, and for preparation of the DNA fragments, a horizontal gel (20 cm×15 cm×0.7 cm) was used for electrophoresis at 150 volts for 4 hours or 35 volts for 13 hours. After staining of the gel for 20 minutes with ethidium bromide aqueous solution (0.5 µg/ml), the DNA bands were detected with ultraviolet irradiation. The agarose gel concentrations used were 1.0, 1.5 and 2.0% (w/v) depending on the size of the DNA fragments to be fractionated.

The DNA in the agarose gel was eluted by placing the gel in a dialysis tube filled with 0.1×TAE buffer and applying a voltage, or by extraction from the gel using SUPREC-01 (Takara Shuzo, KK.). The DNA solutions were treated with phenol and then precipitated with ethanol.

The ligation reaction was conducted adding 10 units of T4 enzyme ligase in 30 µl of a reaction solution (67 mM Tris/HCl (pH 7.5), 5 mM MgCl$_2$, 5 mM DTT, 1 mM ATP) containing 0.05-1 µg of DNA fragments and reacting at 16° C. for 12–18 hours, or using a TAKARA Ligation Kit (Takara Shuzo).

The transformation of *E. coli* was accomplished by the calcium chloride method (competent cells of JM109 were purchased for use), and the transformants were selected on the basis of drug resistance (ampicillin or tetracycline). The transformation of the yeast strain K16-57C was accomplished by the lithium acetate method (METHODS IN YEAST GENETICS; A Laboratory Course Manual, Cold Spring Harbor Laboratory Press), and the transformants were selected on the basis of complementation of tryptophan auxotrophy. Transformation of strain TK62 has been described by Sakai et al. (Sakai et al., J. Bacteriol., 173, 7458–7463, 1991).

Measurement of Kex2 activity was according to the method of Mizuno et al. (Mizuno et al., Biochem. Biophys. Res. Commun. 156, 246–254, 1988). That is, 100 µl of Kex2 diluted with 100 mM Tris/HCl (pH 7.0) was added to 100 µl of 200 mM Tris/HCl (pH 7.0) solution containing 2 mM CaCl$_2$, 0.2% (w/v) Lubrol and 100 µM Boc-Leu-Arg-Arg-MCA (Peptide Laboratories, KK.), and the mixture was allowed to stand at 37° C. for 30 minutes. The reaction was terminated by addition of 50 µl of 25 mM EGTA. The fluorescent intensity of the released fluorescent substance (AMC) was measured using a PANDEX FCA system (Model 10-015-1 of Baxter Travenol (excitation wavelength=365 nm, base wavelength=450 nm)). The amount of Kex2 which released 1 pmol of AMC in one minute under the conditions described above was defined as 1 U.

The SDS-polyacrylamide electrophoresis (SDS-PAGE) was carried out according to the method of Laemmli (Laemmli et al., Nature 227, 680–685, 1970). That is, a ¼ volume of 4×SDS sample buffer (375 mM Tris/HCl (pH 6.8), 30% (v/v) glycerol, 7% (w/v) SDS, 15% (v/v) 2-mercaptoethanol, 0.1% (w/v) bromphenol blue) was added to the sample, and the mixture was heated at 90° C. for 5 minutes. A 10 µl portion was supplied to an SDS-polyacrylamide gel (55 mm×85 mm×1 mm or TEFCO Co.) for electrophoresis at 20 mA for 80 minutes. After electrophoresis, the gel was stained with a staining solution (10% (v/v) acetic acid, 40% (v/v) methanol, 0.25% (w/v) Coomassie brilliant blue R250).

The rest of the basic gene manipulation, except where otherwise stated, was conducted according to the method described in Molecular Cloning (ed. Maniatis et al., Cold Spring Harbor, Cold Spring Harbor Laboratory, New York, 1982).

Reference Example 1

Preparation of chimeric protein βGal-139S(FM) PPH84

1) Construction of hProPTH(1-84) gene (FIGS. 1 and 2)

The hProPTH(1-84) gene was synthesized as the 14 fragments U1 to U7 (SEQ ID NOS.5 to 11) and L1 to L7 (SEQ ID NOS.12 to 18), as shown in FIG. 1.

The hProPTH(1-84) gene was constructed by linking each of the fragments in the following manner (FIG. 2). First, the DNA fragments U1 (SEQ ID NO.5) and L7 (SEQ ID NO.18) (about 1 µg each) were reacted at 37° C. for 15 minutes in 15 µl of a phosphorylation reaction solution (50 mM Tris/HCl (pH 7.6), 10 mM MgCl$_2$, 5 mM DTT) containing 16 units of T4 polynucleotide kinase and 0.5 nM (over 1 MBq) of [γ-$^{32}$P]DATP. To this there was added 5 µl of a phosphorylation reaction solution containing 5 mM ATP, and further reaction was conducted at 37° C. for 45 minutes. The same procedure was followed for U2 (SEQ ID NO.6) and L6 (SEQ ID NO.17), U3 (SEQ ID NO.7) and L5 (SEQ ID NO.16), U4 (SEQ ID NO.8) and L4 (SEQ ID NO.15), U5 (SEQ ID NO.9) and L3 (SEQ ID NO.14), U6 (SEQ ID No.10) and L2 (SEQ ID NO.13) and U7 (SEQ ID NO.11) and L1 (SEQ ID NO.12).

The aforementioned 7 reaction solutions were pooled into one, and ethanol precipitation was performed to recover the DNA. This was dissolved in an 80 µl solution of 100 mM Tris/HCl (pH 7.6), 6.5 mM MgCl$_2$ and 300 mM NaCl. After allowing 40 µl thereof to stand at 95° C. for 5 minutes, the temperature was lowered to 43° C. over 30 minutes. After cooling on ice, 40 µl of ligation B solution (Takara Shuzo, KK.) was added and the mixture was allowed to stand at 26° C. for 15 minutes.

The sample was subjected to 5% polyacrylamide electrophoresis. After electrophoresis, the linked DNA fragments were detected by autoradiography. A DNA fragment corresponding to approximately 280 bp was extracted from the gel and purified according to an established method.

2) Construction of the βGal-139S(FM)PPH84-expressing plasmid pGP#19 (FIGS. 3 and 4)

The approximately 280 bp DNA fragment containing the synthetic hProPTH(1-84) gene includes the restriction enzyme EcoRI site at the 5'-end and the restriction enzyme SalI site at the 3'-end. Cloning of the hProPTH(1-84) gene was accomplished by inserting this EcoRI/SalI DNA fragment at the EcoRI/SalI site of pG210ShCT[G].

After cleaving pG210ShCT[G] with restriction enzymes EcoRI and SalI, an approximately 3.5 kb DNA fragment containing the vector portion was prepared. This was linked with the approximately 280 bp DNA fragment of the hProPTH(1-84) gene obtained in 1) above, to obtain plasmid pG210ShProPTH (FIG. 3). pG210ShProPTH was used to transform E. coli JM109, obtaining JM109 [pG210ShProPTH].

Also, the linkers KM091 (SEQ ID NO.19) and KM092 (SEQ ID NO.20) were inserted at the restriction enzyme XhoI/EcoRI site of pG210ShProPTH, to construct plasmid pG210S(S/X) (FIG. 3). This linker has the restriction enzyme XhoI and EcoRI sites at either end, and a SacI site between them.

After digesting plasmid pG210S(S/X) with restriction enzymes SacI and XhoI, a Kilo-Sequence Deletion Kit (Takara Shuzo, KK.) was used for time-dependent specific deletion of the DNA region coding for βGal-210S. After modification of the ends with Klenow fragment, self-ligation was performed to obtain plasmid pGP#19 coding for the chimeric protein βGal-139S(FM)PPH84 which has βGal-139S and hProPTH(1-84) linked via Phe-Met (FIG. 4). E. coli JM109 having pGP#19 introduced therein is named JM109[pGP#19].

3) Preparation of chimeric protein βGal-139S(FM)PPH84

JM109[pGP#19] was seeded in a 1 L Erlenmeyer flask containing 200 ml of SB medium and cultured at 37° C. with shaking for 16 hours. The total preculturing solution was transferred into 3 L of NU medium containing 10 μg/ml tetracycline, and aerobically shake cultured at 37° C. using a 5 L fermenter (Model KMJ-5B-4U-FP, product of Mitsuwa Physicochemical Industries, KK.) The aeration volume was 3 L/min and the shaking speed was adjusted so that the amount of dissolved oxygen remained over 2.0 ppm.

The pH was kept at pH 7 using 9% (v/v) ammonia water and 1M phosphoric acid. The carbon source provided was glycerol added at 10 ml per 1 L of culture solution on the 3rd, 9th and 14th hours after the start of culturing, and the nitrogen source was a 5-fold concentration of SB medium added at 10 ml per 1 L of culture solution at 9.5 hours after the start of culturing. An antifoaming agent (Disfoam CC-222, Nihon Yushi, KK.) was added at 300 μl/L at the start of culturing, and was added thereafter as necessary.

The OD660 after 18 hours of culturing was 55, and about 0.5 mg of the chimeric protein βGal-139S(FM)PPH84 was produced per ml of culture solution. The chimeric protein was produced as an insoluble inclusion bodies, which was purified in the following manner. A 1.5 L portion of culture solution was subjected to centrifugation at 6000 rpm, 4° C. for 10 minutes (20PR-52D, product of Hitachi Laboratory, KK.), and the cells were collected. The cells were suspended in 320 ml of 100 mM Tris/HCl (pH 7.0) and disrupted with a french cell pressure press (twice at 10,000 psi).

The disrupted cell solution was centrifuged at 4000 rpm, 4° C. for 15 minutes (05PR-22, product of Hitachi Laboratory, KK.: 50 ml plastic tube, product of Sumitomo Bakelite, KK.). After suspending the precipitate in 30 ml of 20 mM Tris/HCl (pH 7.0) containing 0.5% (w/w) TritonX-100, the suspension was centrifuged at 3000 rpm, 4° C. for 15 minutes, and the precipitate was recovered. This procedure was repeated 4 times to obtain the prepurified chimeric protein.

The purity of the prepurified chimeric protein was approximately 70% (estimated by SDS-PAGE), and the amount of protein was about 670 mg (assayed by the Bradford method using bovine serum albumin as the standard).

The prepurified chimeric protein was subjected to high performance liquid chromatography (HPLC: Waters 660E by Millipore, KK.) using a YMC Packed column (2 cm×25 cm, product of Yamamura Chemical Laboratory) for purification. The chimeric protein was eluted with a linear concentration gradient of acetonitrile (A: 0.1% (v/v) trifluoroacetic acid (TFA); B: 0.1% (v/v) TFA/80% (v/v) acetonitrile; %B=30%→60%/60 minutes, flow rate=10 ml/min). Each of the fractions was subjected to SDS-PAGE, and the fractions of 95% purity or greater were pooled and lyophilized.

The lyophilized chimeric protein was again dissolved in 0.1% (v/v) TFA, and then subjected to HPLC for further purification. (The conditions were the same except that the gradient was %B=40%→60%/60 minutes.) The fractions of 99% purity or greater were collected based on the index of absorbance at 210 nm according to analysis by analyzing HPLC, and were lyophilized into a standard. The amount of protein in the standard was estimated from amino acid analysis.

Reference Example 2

Preparation of the soluble chimeric protein CATPH34

Figure 5:
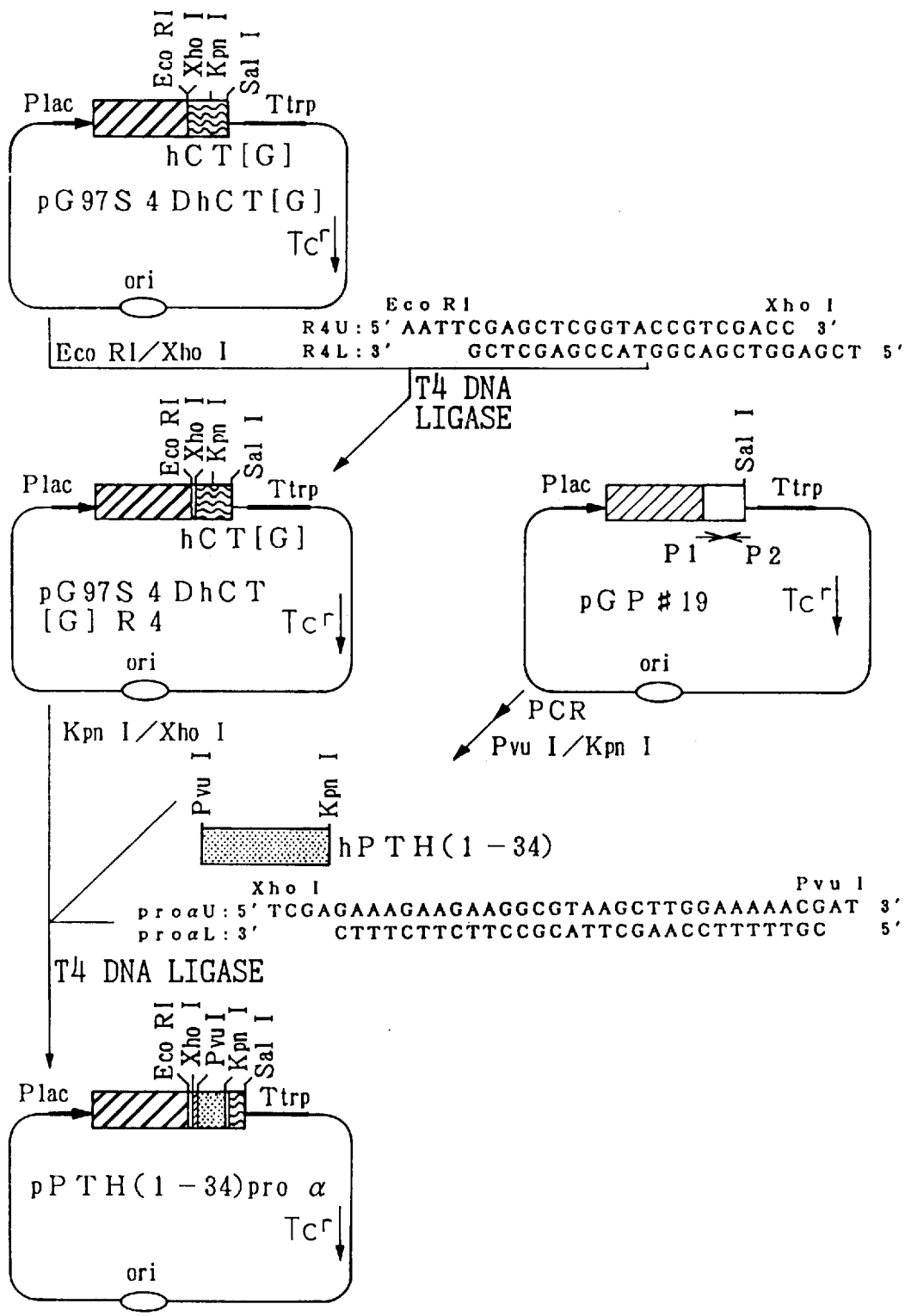
FIG. 5 shows a process for constructing plasmid pPTH (1-34)proα.
Figure 6:
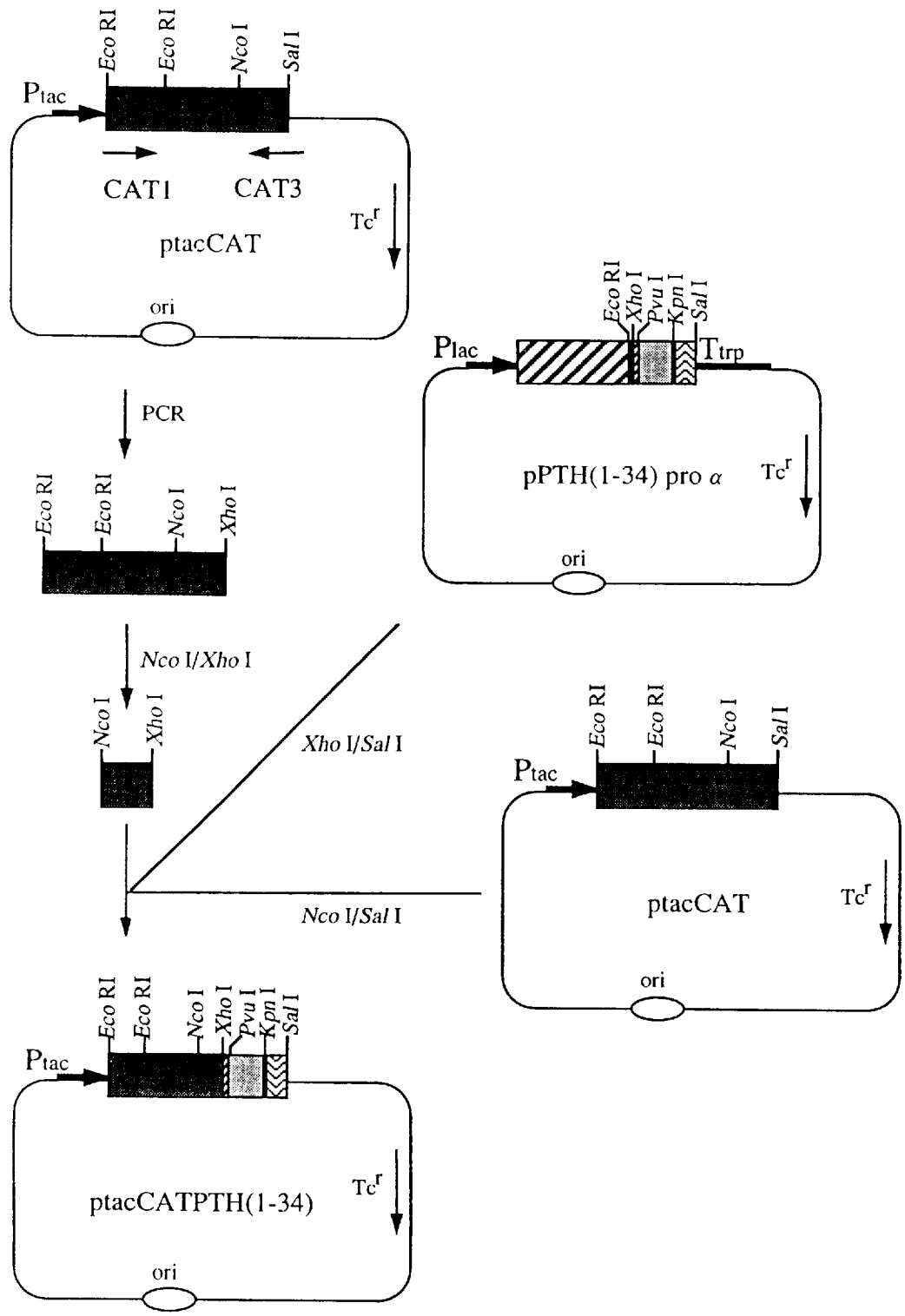
FIG. 6 shows a process for constructing plasmid ptacCATPTH(1-34) which expresses the chimeric protein CATPH34. Ptac represents a synthetic promoter of the −35 region of trp promoter and the −10 region of Plac.

1) Construction of the CATPH34-expressing plasmid ptacCATPTH(1-34) (FIGS. 5 and 6)

An R4 linker (R4U: SEQ ID NO.21 and R4L: SEQ ID NO.22) was inserted at the restriction enzyme EcoRI-XhoI site of pG97S4DhCT[G] to construct pG97S4DhCT[G]R4. The PTH(1-34) gene prepared by PCR and the proα linker described below (proαU: SEQ ID NO.23 and proαL: SEQ ID NO.24) were inserted at the restriction enzyme XhoI-KpnI site of the obtained plasmid pG97S4DhCT[G]R4, to construct pPTH(1-34)proα. The PTH(1-34) gene was prepared by PCR with pGP#19 as the template, using primers P1 (SEQ ID NO.25) and P2 (SEQ ID NO.26) (FIG. 5).

Next, primers CAT1 and CAT3 (SEQ ID NOS.27 and 28) were synthesized in order to insert the restriction enzyme XhoI site at the 3'-end of the CAT (chloramphenicol acetyltransferase) gene. The CAT gene having the restriction enzyme XhoI site inserted at the 3'-end thereof was obtained by PCR using CAT1 and CAT3 as the primers and ptacCAT as the template DNA. This was digested with restriction enzymes NcoI and XhoI, after which the ptacCAT-derived SalI-NcoI DNA fragment (3.6 kbp) and the pPTH(1-34) proα-derived XhoI-SalI DNA fragment (0.15 kbp) were linked to construct ptacCATPTH(1-34) (FIG. 6).

Figure 7:
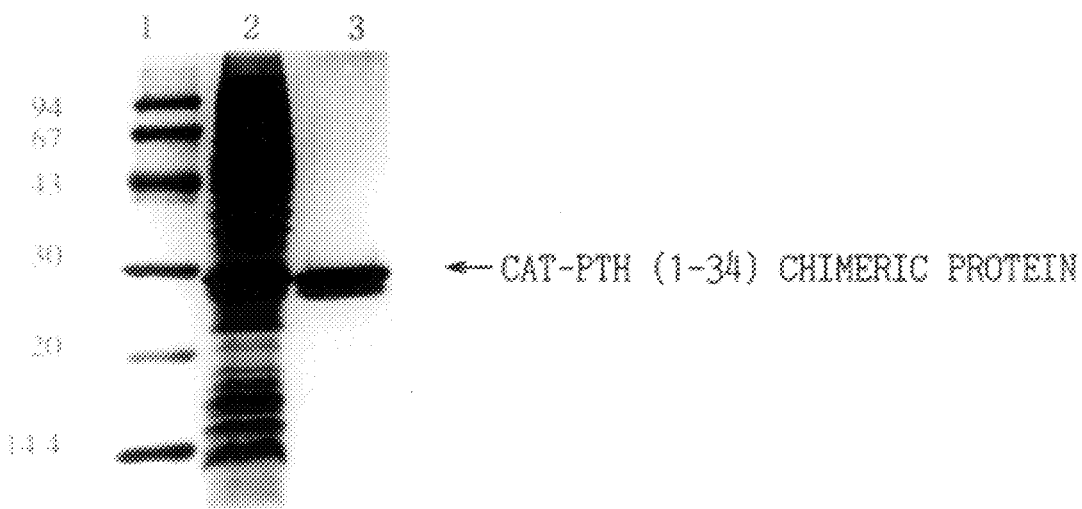
FIG. 7 is a photograph of SDS-PAGE for a sample of the chimeric protein CATPH34 expressed by *E. col*, before and after purification.

2) Preparation of chimeric protein CATPH34 (see FIG. 7).

Strain JM101 containing ptacCATPTH(1-34) was cultured in LB medium at 37° C. IPTG (isopropyl betathiogalactoside) was added to a final concentration of 2 mM when the OD660 value of the culture solution reached 0.6, and culturing was continued for 3 hours to produce the chimeric protein CATPH34. After completion of the culturing, centrifugation (8000 rpm, 20 minutes) was performed to collect the cells, and solution A (50 mM Tris/HCl (pH 8.0), 2 mM EDTA, 0.1 mM 2-mercaptoethanol, 0.1 mM PMSF) was added until the OD660 value of the suspension reached 70.

Next, 3 ml of the cell suspension was subjected to ultrasonic treatment, and after disruption of the cells, the soluble fraction was separated by centrifugation (12,000 rpm, 10 minutes), and applied to a chloramphenicol caproate (Sigma C-8899) column (3 ml) equilibrated with solution A. After washing the column with solution A containing 1M NaCl, the chimeric protein was eluted with solution A containing 10 mM chloramphenicol and 1M NaCl. FIG. 7 shows the results of SDS-PAGE for samples before and after purification. Lane 1 is the molecular weight marker, lane 2 is the soluble fraction after cell disruption, and lane 3 is the chimeric protein CATPTH(1-34) after purification. The numbers to the left of lane 1 indicate the sizes of the molecular weight markers (kDa).

The chimeric protein was produced in the soluble fraction, and was easily purified by affinity chromatography using chloramphenicol caproate.

Reference Example 3

Preparation of insoluble chimeric protein βGal-117S4HPPH34

Figure 8:
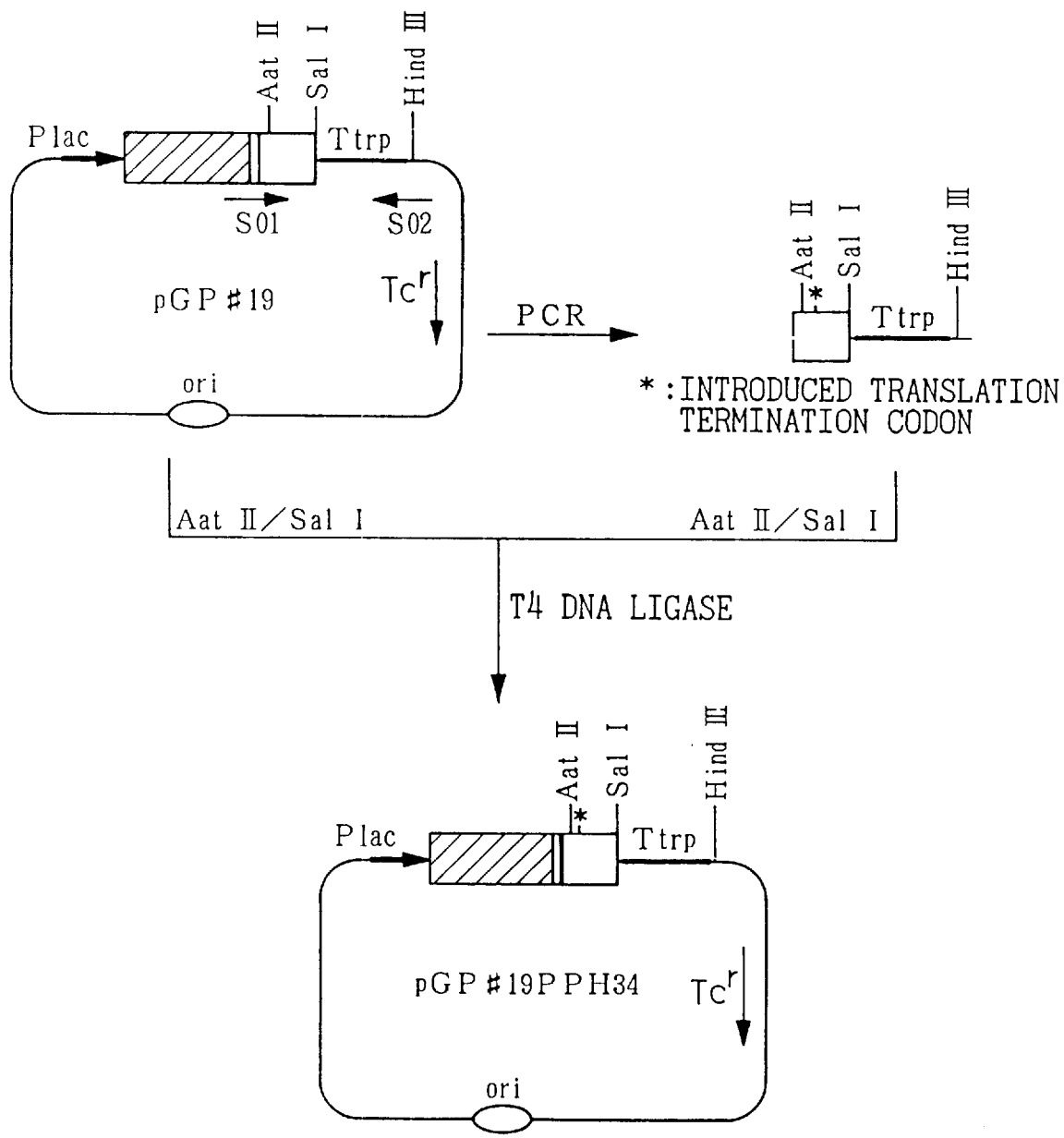
FIG. 8 shows a process for constructing plasmid pGP#19PPH34 which expresses the chimeric protein βGal-139SPPH34.
Figure 9:
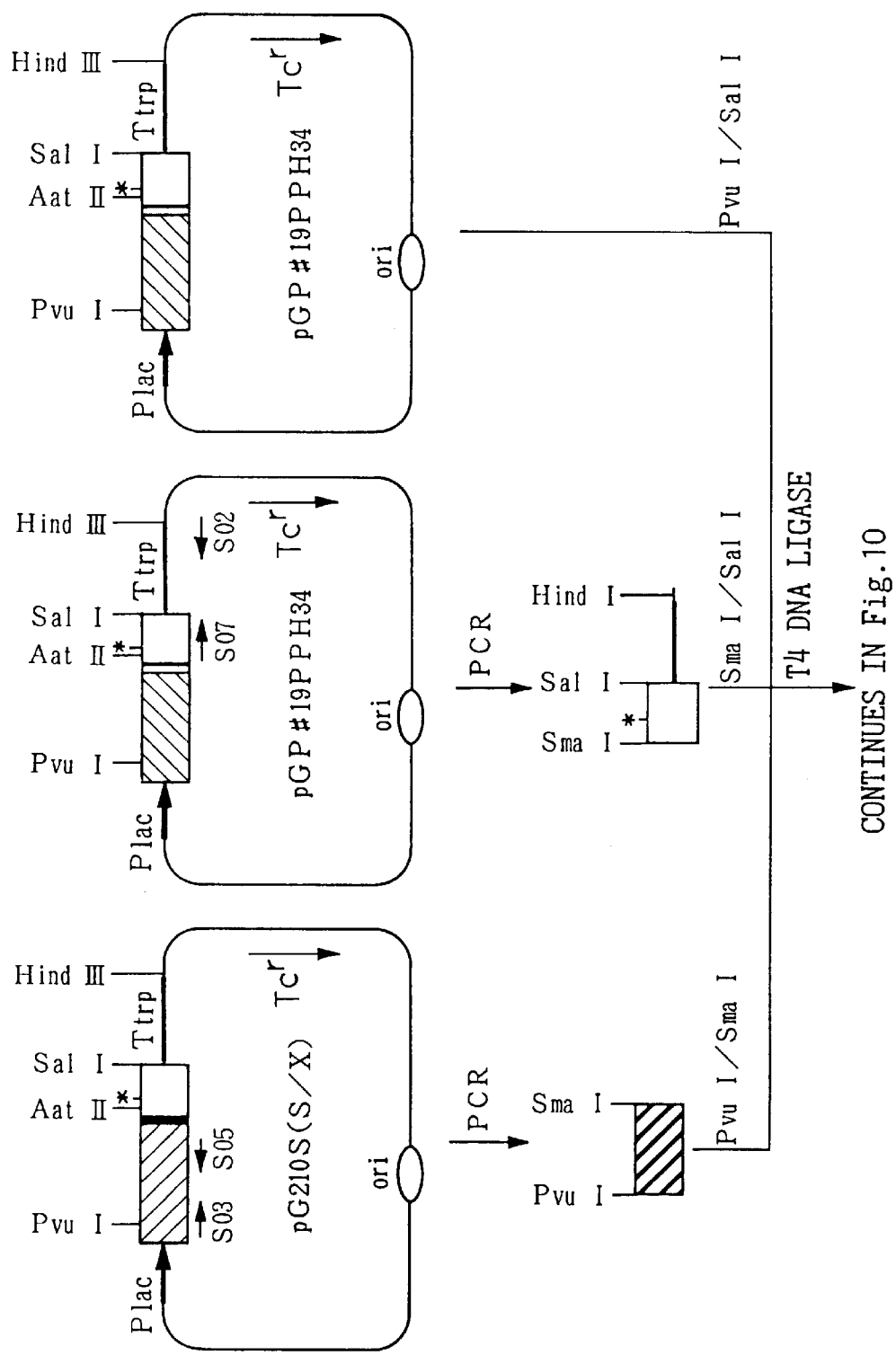
FIG. 9 shows the former steps in a process for constructing plasmid pG117S4HPPH34 which expresses the chimeric protein βGal-117S4HPPH34.
Figure 10:
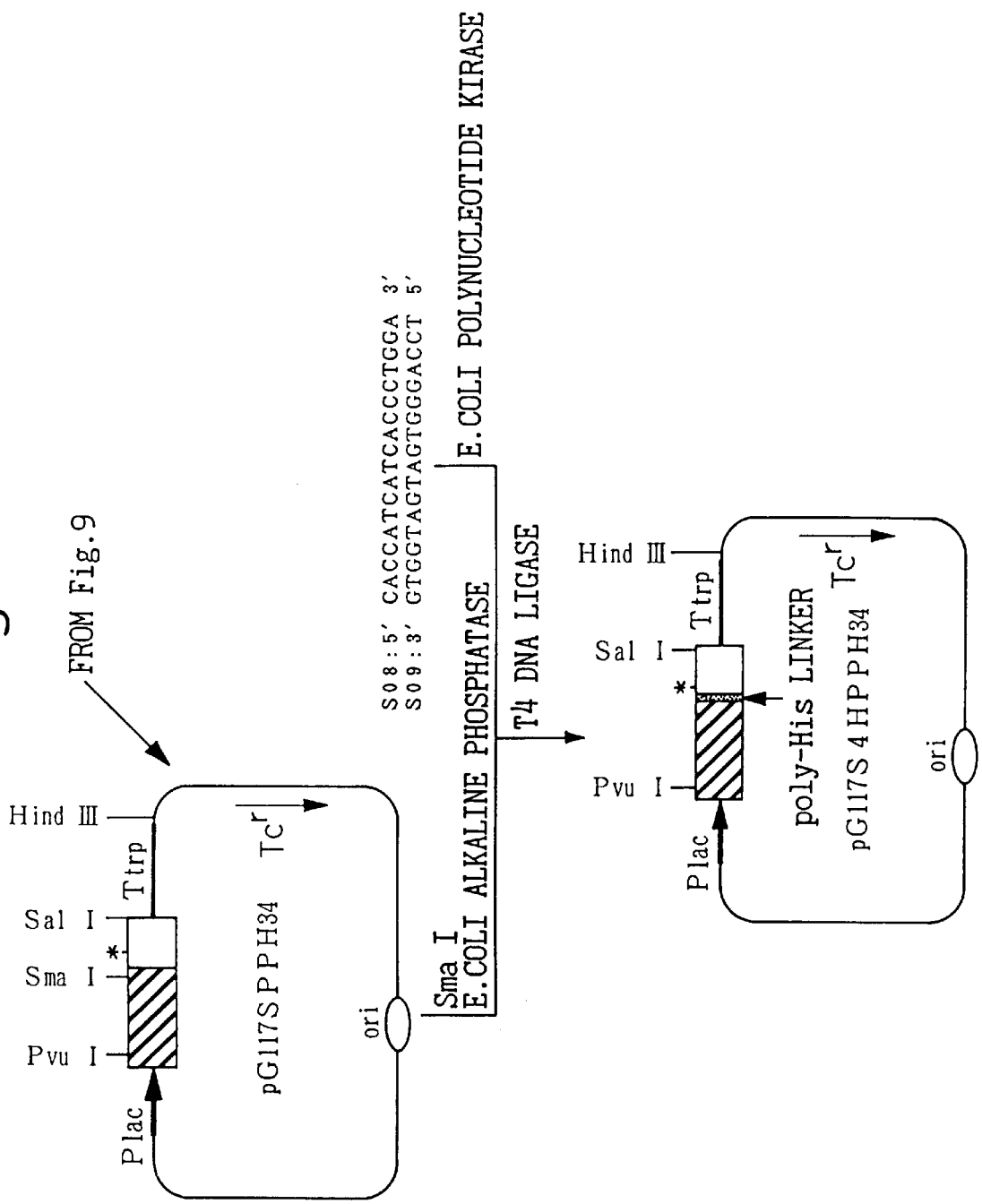
FIG. 10 shows the latter steps in the process for constructing plasmid pG117S4HPPH34 which expresses the chimeric protein βGal-117S4HPPH34.

1) Construction of the βGal-117S4HPPH34-expressing plasmid pG117S4HPPH34 (FIGS. 8 to 10)

pGP#19 was used as the template and S01 (SEQ ID NO.29) and S02 (SEQ ID NO.30) as primers for PCR to amplify a DNA fragment in which the 35th codon GTT of hPTH(1-84) was replaced with the translation termination codon TAA, after which the restriction enzyme AatII-SalI DNA fragment was isolated and purified by common methods and exchanged with the corresponding portion of pGP#19 to construct pGP#19PPH34 (FIG. 8).

Next, a DNA fragment obtained by amplification by PCR using pG210S(S/X) as the template and S03 (SEQ ID NO.31) and S05 (SEQ ID NO.32) as the primers followed by digestion with restriction enzymes SalI and SmaI, a DNA fragment obtained by amplification by PCR using pGP#19PPH34 as the template and S07 (SEQ ID NO.33) and S02 (SEQ ID No.30) as the primers followed by digestion with restriction enzymes SalI and SmaI and a restriction enzyme PvuI-SaiI DNA fragment containing the replication initiation origin of pGP#19PPH34 were linked with T4 ligase, to construct pG117SPPH34 (FIGS. 9 to 10).

Linkers S08 (SEQ ID NO.34) and S09 (SEQ ID NO.35) coding for (His)$_4$-Pro-Gly were inserted at the restriction enzyme SmaI site of pG117SPPH34 to construct pG117S4HPPH34 (FIG. 10). The orientation of the linkers was confirmed by determining the DNA nucleotide sequences after preparing the plasmids.

2) Production of chimeric protein βGal-117S4HPPH34

To obtain the chimeric protein βGal-117S4HPPH34 in a large amount, E. coli M25[pG117S4HPPH34] in which the expression vector for the chimeric protein had been introduced was cultured at 37° C. in a 20 L SB2 medium. With a cell concentration of OD660=1.0, IPTG was added to a final concentration of 1 mM, and culturing was continued until the cell concentration reached OD660=12. Disfoam CC-222 (product of Nihon Yushi, KK.) was used as an antifoaming agent. After collecting the cells, they were suspended in TE (10 mM Tris/HCl, 1 mM EDTA, pH 8.0), and this was followed by cell disruption with a high-pressure homogenizer (Manton-Gaullin), centrifugation, and suspension and washing with TE and deionized water, to obtain about 100 g of an inclusion bodies.

Example 1

Expression of secretory Kex2 derivatives in Saccharomyces cerevisiae

For purification of a large amount of enzymes with Kex2 protease activity, not only must the yields be high, but the purification thereof must also be simple, and for this purpose the inventors considered it advantageous to carry out secretion in a culture solution containing few other proteins. Although ssKex2 has been reported as a secretory Kex2 derivative, its yield is 4 mg/L culture solution which is too low for use on an industrial scale. Thus, different secretory Kex2 derivatives were constructed first, and were expressed in Saccharomyces cerevisiae to investigate the secretion yields, selecting among them the Kex2 derivatives with the greatest secretion yields.

Figure 11:
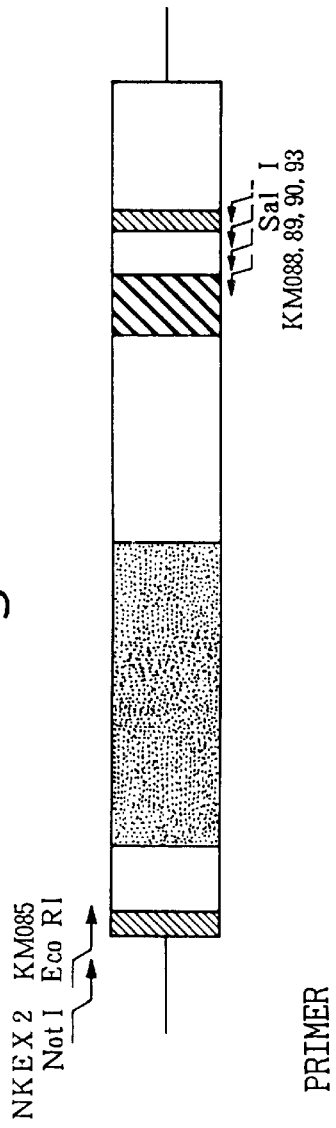
FIG. 11 shows the structure of the KEX2 gene and the sequences of the primers synthesized for construction of the secretory Kex2 derivative genes, and their respective annealing sites.

1) Construction of secretory Kex2 derivative-expressing plasmids (FIGS. 11, 12 and 13)

The secretory KEX2 gene was constructed by the PCR. The primer sequence is shown in FIG. 11(b). KM085 (SEQ ID NO.36) has the restriction enzyme EcoRI site (underlined) at the 5'-end, and KM088 (SEQ ID NO.37), KM089 (SEQ ID NO.38), KM090 (SEQ ID NO.39) and KM093 (SEQ ID NO.40) have the restriction enzyme SalI site (underlined) at their 5'-ends.

These primers correspond to the KEX2 gene region shown in FIG. 11(a), with KM085 including a nucleotide sequence coding for the initial methionine of the KEX2 gene, and KM088, KM089, KM090 and KM093 having nucleotide sequences which are antisense to sequences in which the translation termination codon TAA is added directly to the 660th, 679th, 688th and 699th amino acids from the N-terminus, respectively.

A PCR reaction was conducted using plasmid pYE-KEX2 (5.0)b, cut with restriction enzyme EcoRI and in linear form as template, using KM085 and KM088 as primers. The reaction purification product was cleaved with restriction enzymes EcoRI and SalI to obtain an EcoRI-SalI DNA fragment. This DNA fragment has the DNA nucleotide sequence coding for Kex2-660 (KEX2-660), with the restriction enzyme EcoRI site upstream and the restriction enzyme SalI site downstream.

Next, after cleaving plasmid pYE-22m with restriction enzymes EcoRI and SaiII, the approximately 8.3 kb DNA fragment containing the vector portion was purified. This was linked with the EcoRI-SalI DNA fragment containing the gene coding for Kex2-660 obtained earlier, to obtain plasmid pYE-660 (FIG. 12).

In the same manner, KM089, KMO90 and KM093 were used instead of the primer KM088, the EcoRI-SalI DNA fragments containing nucleotide sequences coding for Kex2-679, Kex2-688 and Kex2-699 (KEX2-679, KEX2-688, KEX2-699) were recovered and linked with the EcoRI-SalI fragment of plasmid pYE-22m, to obtain plasmids pYE-679, pYE-688 and pYE-699.

Plasmid pYE-614 was constructed by replacing the BglII-SalI DNA fragment containing a portion of the KEX2 gene of pYE-KEX2 (RI-PvuII) with the BglII-SalI DNA fragment containing a portion of the KEX2-660 gene of pYE-660 (FIG. 13).

Figure 14:
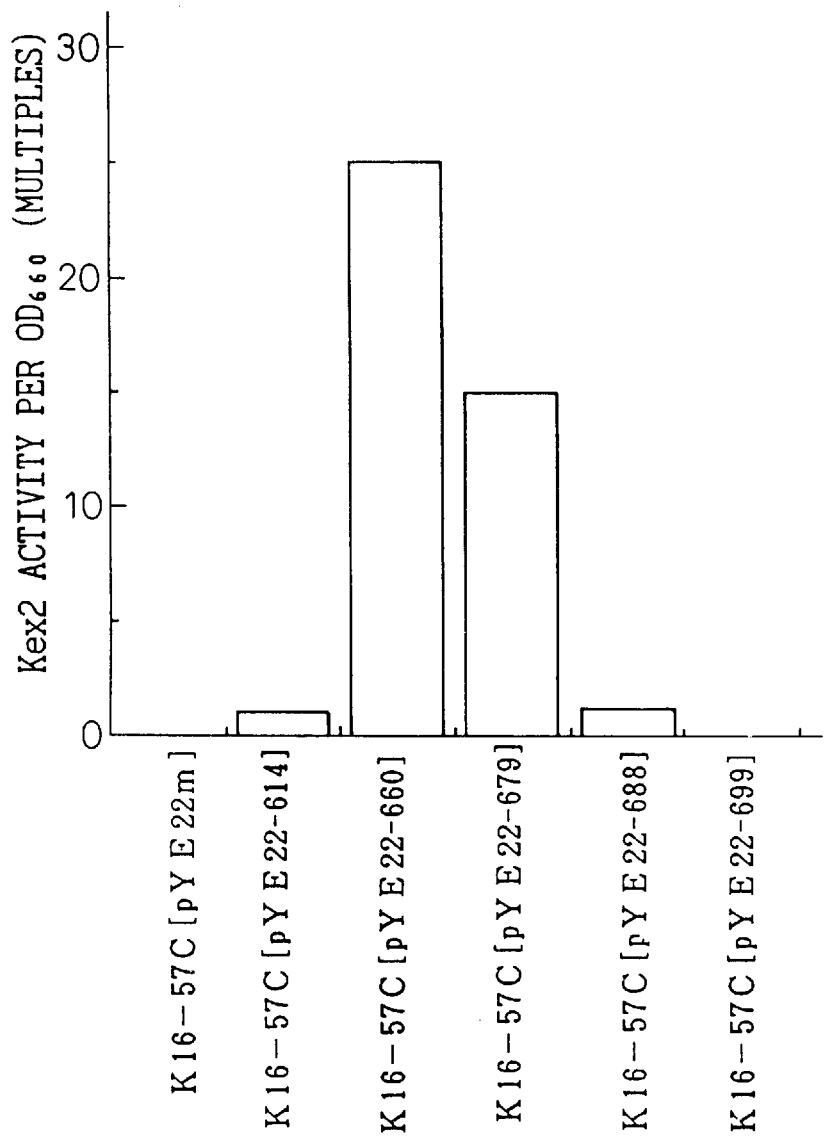
FIG. 14 is a graph comparing Kex2 activity per OD660 of secretory Kex2 derivatives using a synthetic substrate. The relative activities of the cultures of secretory Kex2 derivative producing strains are given taking the activity of K16-57C[pYE-614] as 1.
Figure 15:
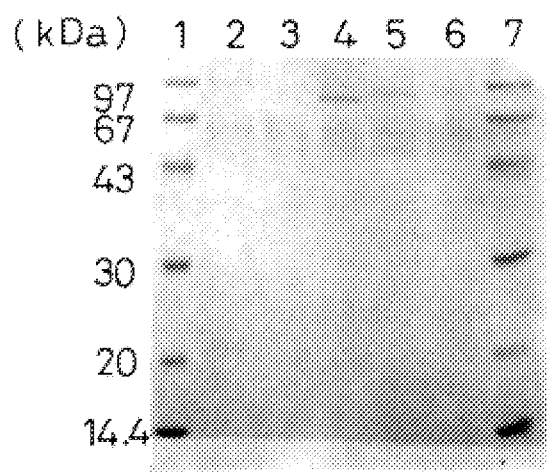
FIG. 15 is a photograph of an electrophoresis which gives a comparison of yields per 200 μl of culture supernatant of secretory Kex2 derivatives.

2) Transformation and expression of secretory Kex2 derivatives (see FIGS. 14 and 15)

The plasmids (pYE-22m, pYE-614, pYE-660, pYE-679, pYE-688 and pYE-699) were each introduced in strain K16-57C to obtain strains K16-57C[pYE-22m], K16-57C [pYE-614], K16-57C[pYE-660], K16-57C[pYE-679], K16-57C[pYE-688] and K16-57C[pYE-699].

The amounts of Kex2 derivative secretion in the culture solutions were determined by assay of Kex2 activity in the culture supernatants and SDS-PAGE of their concentrates.

The colonies were seeded into 4 ml of YCDP medium and then cultured overnight at 32° C. with shaking. After transferring 100 μl of culture solution to 4 ml of YCDP medium, it was cultured overnight at 32° C. with shaking. One ml of the culture solution was centrifuged at 12,000 rpm, 5 minutes, 4° C. (MRX-150, Tomy Seiko) to obtain the culture supernatant. After diluting the culture supernatant 2- to 64-fold with 100 mM Tris/HCl (pH 7.0), the Kex2 activity was measured. The results are shown in FIG. 14. The Kex2 activities per OD660 of K16-57C[pYE-660], K16-57C [pYE-679] and K16-57C[pYE-688] were 25, 15 and 1.2 times greater, respectively, than that of K16-57C[pYE-614]. No Kex2 activity was detected in the culture supernatants of K16-57C(pYE-22m] and K16-57C[pYE-699].

The samples for SDS-PAGE were prepared by concentrating the culture supernatants to 20-fold using an Ultrafree-C3GC (Millipore, KK.; fractionation molecular weight=10, 000), and approximately 200 μl of culture supernatant was used per lane. The results are shown in FIG. 15. Lanes 1 and 7 are molecular weight markers, lane 2 is for K16-57C[pYE-22m], lane 3 is for K16-57C[pYE-614], lane 4 is for K16-57C[pYE-660], lane 5 is for K16-57C[pYE-679] and lane 6 is for K16-57C(pYE-688]. The numbers to the left of lane 1 indicate the sizes of the molecular weight markers (kDa).

It was shown that Kex2-660 and Kex2-679 had greater secretion amounts than Kex2-614, similar to their activities. It was also shown that their molecular weights increased correspondingly with the number of amino acid residues, i.e. that no autolysis accumulated in this culturing as occurs with Kex2Δp in the insect cell host Sf9.

The secretory yields of Kex2-660 and Kex2-679 were found to be much greater, at least 10 times greater, than the secretory yield of Kex2-614 hitherto reported. Also, since no notable autolysis was observed in the culture supernatants, even higher yields may be expected by investigating other methods of production.

Example 2

Purification of Kex2-660

Culturing of K16-57C[pYE-660] was carried out on a greater scale, with the object of purifying Kex2-660 from the culture supernatant.

K16-57C[pYE-660] was cultured overnight at 32° C. in 3 L of YCDP medium. A 2.3 L portion of the culture supernatant was subjected to concentration and exchange of the buffer solution (20 mM Bis-Tris/HCl (pH 6.0), 50 mM NaCl, 0.2 mM $CaCl_2$), using an ultrafiltration module (UF-LMSII System: UF2CS-3000PS, Toso, KK.) (final volume: 275 ml).

A 210 ml portion thereof was adsorbed onto a Q-Sepharose XK16 (Pharmacia, KK.) column equilibrated beforehand with the same buffer solution. After washing with 75 ml of the same buffer solution, elution (120 ml) was performed in the same buffer solution with a linear concentration gradient of 50 to 350 mM NaCl concentration. The flow rate was 3 ml/min. Kex2 activity was recovered in 24 ml of eluted fractions of 150 to 250 mM NaCl concentration. After adding 6.6 g of ammonium sulfate to the eluate, 1N HCl was used to adjust the pH to 6.0, and the volume was increased to 30 ml with 20 mM Bis-Tris/HCl (pH 6.0), 0.2 mM $CaCl_2$.

A 15 ml portion thereof was adsorbed onto a Phenyl Superose HR 5/5 (Pharmacia) column equilibrated beforehand with a 20 mM Bis-Tris/HCl (pH 6.0), 0.2 mM $CaCl_2$ solution containing 2M ammonium sulfate. After washing with 2.5 ml of the same buffer solution, elution (15 ml) was performed in 20 mM Bis-Tris/HCl (pH 6.0), 0.2 mM $CaCl_2$ with a linear concentration gradient of 2 to 0M ammonium sulfate. The flow rate was 0.5 ml/min. Kex2 activity was recovered in 2.25 ml of eluted fractions of 0.8 to 0.6M ammonium sulfate concentration. The recovery rates of Kex2-660 at each stage are shown in Table 1. The overall recovery rate was determined by integrating the recovery rates at each stage.

TABLE 1

| | Kex2-660 purification | | |
|---|---|---|---|
| | Activity | Recovery rate (%) | |
| Stage | ($\times 10^4$ U/ml) | *1 | *2 |
| Culture supernatant | 9.3 | | 100 |
| 0.22 μm filtration | 9.2 | 99 | 99 |
| Ultrafiltration | 50 | 99 | 97 |
| Q-Sepharose | 250 | 63 | 61 |
| Phenyl Superose | 1,740 | 93 | 57 |

*1: Recovery rate at each stage
*2: Recovery rate from culture supernatant sample Example 3

Effect of urea on Kex2 protease activity of Kex2-660

In chimeric protein expression process, the chimeric protein usually forms insoluble inclusion bodies, and thus urea or the like is used as a denaturing agent to solubilize it. The effect of urea on the activity of Kex2 protease and secretory Kex2 derivatives has not been reported. Thus, we determined the effect of urea on protease activity of Kex2-660 using Boc-Leu-Arg-Arg-MCA and the chimeric protein βGal-139S(FM)PPH84 as substrates.

Figure 16:
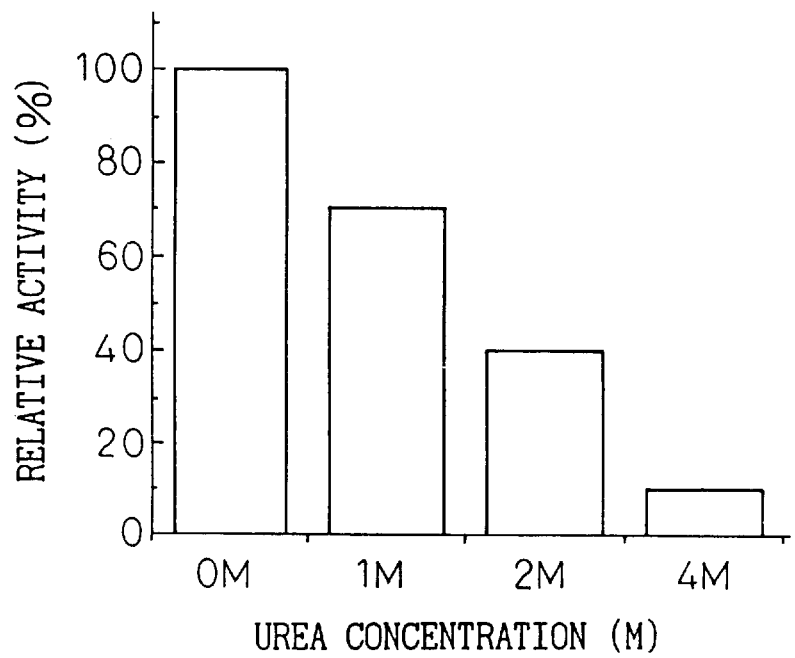
FIG. 16 is a graph showing the activities of Kex2-660 at different urea concentrations, using the synthetic substrate Boc-Leu-Arg-Arg-MCA. The relative activities at each urea concentration are given taking the Kex2-660 activity in the absence of urea as 100%.

1) Effect of urea on Kex2 protease activity of Kex2-660 with synthetic substrate The activities of the Kex2-660 purified in Example 2 (adjusted to a final concentration of 80 to 1200 U/ml) with final urea concentrations of 0, 1, 2 and 4M was investigated using Boc-Leu-Arg-Arg-MCA. The reaction conditions were the same as the Kex2 activity assay method described earlier, except for urea. The activities at urea concentrations of 1, 2 and 4M were found to be 70%, 40% and 10%, respectively, with respect to 100% activity in the absence of urea (FIG. 16). For activation of protease, etc. after dissolving the insoluble inclusion bodies in urea solution, a 2 to 4M urea concentration is generally used. Thus, it was concluded that Kex2-660 can be used for excision of desired peptides from chimeric proteins, if the dissolution conditions of the chimeric proteins are appropriate determined.

2) Effect of urea on Kex2 protease activity of Kex2-660 with protein substrate

The effect of urea on the protease activity of Kex2-660 was investigated using the βGal-139S(FM)PPH84 prepared in Reference Example 1 and the Kex2-660 purified in Example 2. First, reaction was conducted at 37° C. for 30 minutes under the reaction conditions described below, using urea concentrations of 1.5 to 3.0M. After adding a 4-fold volume of 5N acetic acid, 50 μl of the reaction solution was subjected to high performance liquid chromatography (HPLC: LC6A, product of Shimazu Laboratories) using a YMC-ODS-A302 column (d 4.6 mm×150 mm, product of Yamamura Chemical Laboratories), and eluted with a linear concentration gradient (A: 0.1% (v/v) trifluoroacetic acid (TFA); B: 0.094% (v/v) TFA/80% (v/v) acetonitrile; %B 30%→60%/30 minutes, flow rate=1 ml/min).

| | |
|---|---|
| 2 mg/ml | βGal-139S(FM)PPH84 |
| 100 mH | Tris/HCl (pH 7.0) |
| 1.5 to 3.0 M | urea |
| 1 mM | CaCl$_2$ |
| 50 kU/ml | Kex2-660 |

The peaks newly appearing after Kex2-660 processing were divided, and identification and amino acid compositional analysis of the amino acid sequence from the N-terminus identified βGal(1-14), hPTH(1-84) and hPTH (1-44). βGal-139S(FM)PPH84 has 4 sites of sequences predicted to be cleaved by Kex2 protease: Arg-Arg (cleavage site A), Lys-Arg (cleavage site B) and Pro-Arg (cleavage sites C and D). Cleavage at cleavage sites A, B and C was confirmed from the identified peptide fragments, but cleavage at cleavage site D could not be confirmed.

The recovery rates for each of the peptide fragments produced after Kex2-660 processing were determined in the following manner.

Recovery rate(%)=FPA×CAA×100/(CPA x FAA)

FPA: Peak area for each peptide fragment after Kex2-660 processing

CAA: Number of amino acids of βGal-139S(FM)PPH84 (231 amino acids)

CPA: Peak area for BGal-139S(FM)PPH84 before Kex2-660 processing

FAA: Amino acid number of each peptide fragment

Figure 17:
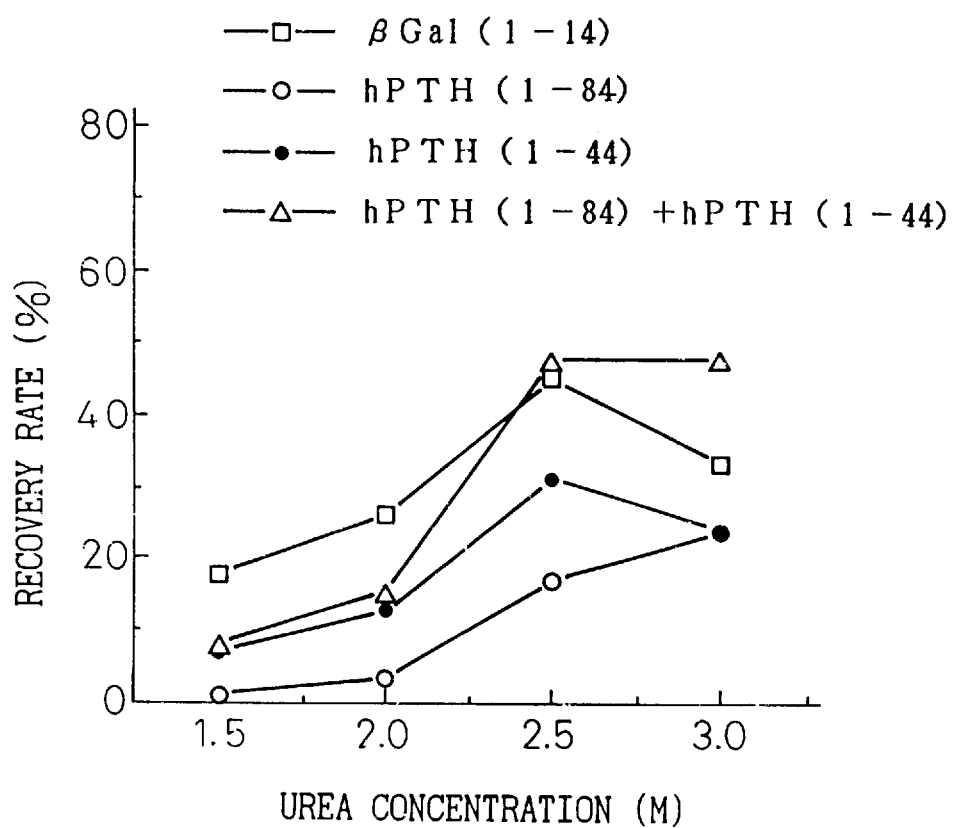
FIG. 17 is a graph comparing the recovery rates of βGal(1-14), hPTH(1-84), hPTH(1-44) and [hPTH(1-84)+hPTH(1-44)] from βGal-139S(FM)PPH84, at different urea concentrations (1.5–3.0M).

The results are shown in FIG. 17. The open squares, open circles, solid circles and open triangles represent, respectively, recovery rates for βGal(1-14), hPTH(1-84), hPTH(1-44) and hPTH(1-84) +hPTH(1-44).

It was shown that in the urea concentration range of 1.5 to 2.5M, an increase in urea concentration resulted in a higher recovery rate of the peptide excised by Kex2-660, i.e. an increase in the cleavage efficiency at cleavage sites A, B and C.

On the other hand, it was found that in the urea concentration range of 2.5 to 3.0M the recovery rate for βGal(1-14) and hPTH(1-44) fell while the recovery rate for [hPTH(1-84)+hPTH(1-44)] was virtually unchanged and that of hPTH (1-84) increased; thus the cleavage efficiency at cleavage site B was unchanged while the cleavage efficiency at cleavage sites A and C fell. In other words, this showed that with cleavage of βGal-139S(FM)PPH84 by Kex2-660, increasing urea concentrations of up to 2.5M give higher cleavage efficiency, while at urea concentrations of 2.5 to 3.0M differences in cleavage efficiency occur depending on the sequence.

The following experiment was then conducted with higher urea concentrations of 3.0 to 4.0M, to determine the peptide fragment recovery rates, etc.

| | |
|---|---|
| 2 mg/ml | βGal-139S(FM)PPH84 |
| 100 mM | Tris/HCl (pH 7.0) |
| 3.0 to 4.0 M | urea |
| 1 mM | CaCl$_2$ |
| 20 kU/ml | Kex2-660 |

Figure 18:
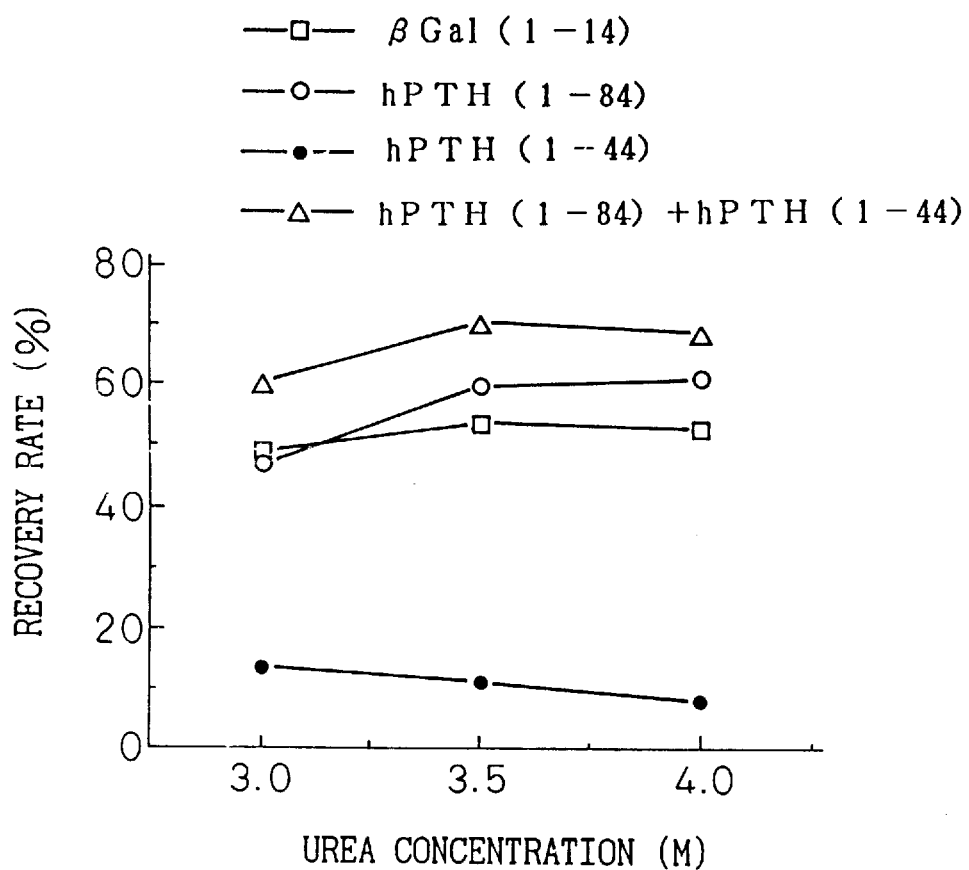
FIG. 18 is a graph comparing the recovery rates of βGal(1-14), hPTH(1-84), hPTH(1-44) and [hPTH(1-84)+hPTH(1-44)] from βGal-139S(FM)PPH84, at different urea concentrations (3.0–4.0M).

The results are shown in FIG. 18. The symbols and calculations for the recovery rates were as explained above.

As a result, no notable difference was observed in the recovery rates of any of the fragments at urea concentrations of 3.0 to 4.0M, although increasing urea concentrations provided lower recovery rates for βGal(1-14) and hPTH(1-44), and a tendency for increased hPTH(1-84) was seen. That is, it was found that with increasing urea concentration the cleavage efficiency at cleavage site B was slightly greater, while the cleavage efficiency at cleavage site C was reduced.

To summarize the results for cleavage of βGal-139S(FM) PPH84 by Kex2-660 at urea concentrations of 1.5 to 4.0M, it was found that increasing urea concentration within a urea concentration range of 1.5 to 2.5M gives greater cleavage efficiency at cleavage sites A, B and C, and in the urea concentration range of 2.5 to 3.5M the cleavage efficiency at cleavage site B increases while the cleavage efficiency at cleavage site C decreases. These discoveries were not predictable from using synthetic substrates, and were first arrived at by the present invention.

From the standpoint of excision of hPTH(1-84) from chimeric proteins, it became clear that a urea concentration of 3.5 to 4.0M is preferred at which the cleavage efficiency at cleavage site B is high and the cleavage efficiency at cleavage site C is low.

Example 4

Excision of hPTH(1-84) from βGal-139S(FM) PPH84 with Kex2-660

In Example 3, βGal(1-14), hPTH(1-84) and hPTH(1-44) were identified and the effect of urea on the cleavage efficiency of βGal-139S(FM)PPH84 by Kex2-660 was investigated based on their peptide recovery rates. However, peptide fragments from hPTH(45-84) could not be identified. Thus, a sample of hPTH(1-84) processed with Kex2-660 was separated and analyzed by HPLC under various elution conditions to identify hPTH(45-84), and it was confirmed that it had eluted out in the fraction which had passed through in elution under the previous conditions. These results demonstrated that cleavage site D undergoes virtually no cleavage.

Next, different proportions of Kex2-660 (25 kU, 50 kU, 100 kU, 150 kU and 200 kU per 1 mg of chimeric protein) were allowed to act on the chimeric protein, and after 30 minutes the recovery rates of each of the peptide fragments were investigated. The analysis of the resulting peptide fragments was carried out in the same manner as in Example 3, except that based on the results mentioned above, the gradient conditions were changed to %B=0%→80%/80 minutes.

| | |
|---|---|
| 1 mg/ml | βGal-139S(FM)PPH84 |
| 100 mM | Tris/HCl (pH 7.0) |
| 4 M | urea |
| 1 mM | CaCl$_2$ |
| 25 to 200 kU/ml | kex2-660 |

Figure 19:
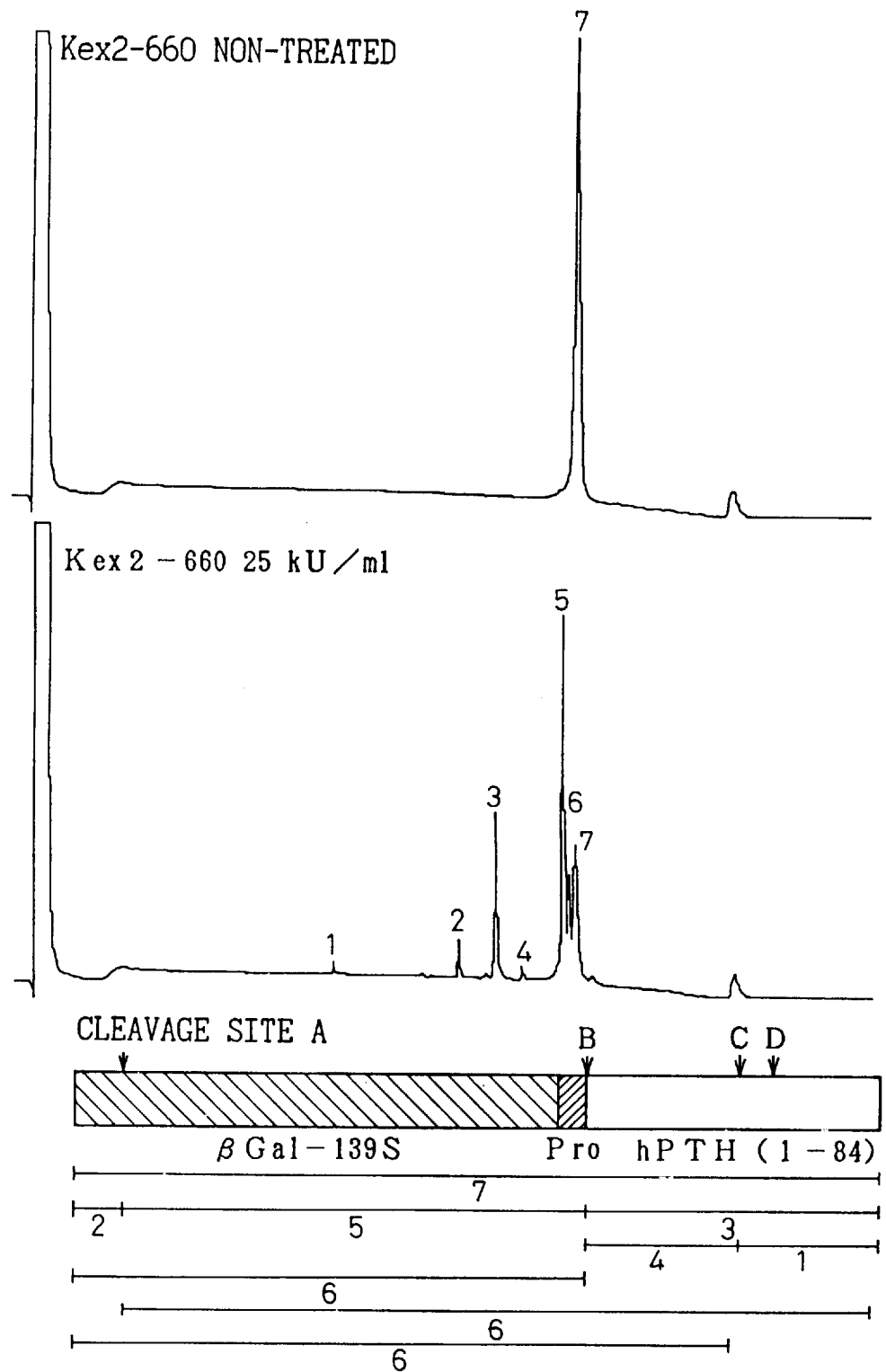
FIG. 19 shows an elution profile of HPLC for before and after Kex2-660 processing of the chimeric protein βGal-139S(FM)PPH84 and a schematic representation of the relationship between identified peptide fragments and βGal-139S(FM)PPH84. The peak numbers in the profile correspond to the numbers of the fragments. Fragments 1, 2, 3 and 4 were identified by determining the amino acid sequences. Fragment 7 was estimated based on elution time, and fragment 5 was estimated by correlation between βGal(1-14) and hPTH(1-84). Fragment 6 was so designated for fragments which may be eluted.

FIG. 19 shows an elution profile of HPLC for samples unprocessed with Kex2-660 and processed with 50 kU of Kex2-660. Peaks 1, 2, 3, 4 and 7 correspond, respectively, to hPTH(45-84) (from the amino acid after cleavage site C to the C-terminus of hPTH(1-84)), βGal(1-14) (from the N-terminus of βGal-139S to cleavage site A), hPTH(1-84), hPTH(1-44) (from the amino acid after cleavage site B to cleavage site C) and βGal-139S(FM)PPH84 (full length of the chimeric protein).

Peaks 6 and 7 were larger when the amount of Kex2 -660 was smaller and smaller when the amount was larger, and since peak 5 increased as peaks 6 and 7 decreased, it was concluded that peak 5 was a peptide from the amino acid after cleavage site A to cleavage site B of the chimeric protein, and peak 6 was a peptide from the N-terminus of βGal-139 to cleavage site B or from the amino acid after cleavage site A to the C-terminus of hPTH(1-84). (Peak 6 may possibly be from the N-terminus of βGal-139S to cleavage site C, but this is unlikely since Arg-Arg is more easily cut than Pro-Arg.)

Also, the sizes of peaks 1, 4, 5, 6 and 7 varied in the range of 25 to 200 kU/ml, while the sizes of peaks 2 and 3 were virtually unchanged. Even when 200 kU/ml of Kex2-660 was used, no new peaks appeared. In other words, it was confirmed that no protease activity other than that of Kex2 protease is detected even when using 8 times (200 kU/ml) the necessary amount of Kex2-660 (25 kU/ml) for excision of hPTH(1-84), and that the Kex2-660 purified in Example 2 had no contamination by other interfering proteases under conditions at which hPTH(1-84) is excised from chimeric proteins.

The recovery rates for the peptide fragments derived from hPTH(1-84) in the range of 25 to 200 kU/ml are summarized in FIG. 20. It is clear that when 50 kU/ml of Kex2-660 was used, hPTH(1-84) was recovered at about 75%. Here, although about 10% of the βGal-139S(FM)PPH84 remained, it decreased as the amount of Kex2-660 increased, almost totally disappearing at 200 kU/ml. However, the proportion of hPTH(1-44) also increased simultaneously, and thus the recovery rate of hPTH(1-84) did not increase. Even when the amount of Kex2-660 was raised, the increase in the hPTH(1-84) decomposition products hPTH(1-44) and hPTH(45-84) was mild, and the recovery rate of hPTH(1-84) was 65–75% in the range of 25 to 200 kU/ml. These results demonstrate that Kex2-660 is capable of excising desired peptides from chimeric proteins in an efficient manner (an excision efficiency of 75%) even when the desired peptide has a cleavage site for Kex2 protease. This excision efficiency is higher than the excision efficiency of 50% for hPTH(1-84) using factor-Xa (Gardella et al., J. Biol. Chem. 265(26), 15854–15859, 1990). Gardella et al. have suggested the possibility that contaminating proteases or factor-Xa itself degrades hPTH(1-84), judging from lower hPTH (1-84) recovery rates when the enzyme amount is increased or the reaction time is extended, despite the fact that hPTH(1-84) does not include the factor-Xa recognition site, i.e. the Ile-Glu-Gly-Arg sequence.

The fact that hPTH(1-84) is obtained at a high yield despite the fact that hPTH(1-84) includes 2 sites of cleavage sequences for Kex2 protease suggests that the purified Kex2 derivatives with increased yields according to the invention are useful as enzymes for excision of desired peptides from chimeric proteins.

Furthermore, since there was no detection of any other peptide fragments produced by cleavage at sites other than the Kex2 protease site even when the amount of Kex2-660 was increased, the substrate specificity of the Kex2 purified in Example 2 is high, while no other protease activity was detected under conditions at which desired peptides are excised from chimeric proteins.

Example 6

Excision of hPTH(1-34) from CATPH34 by Kex2-660

In order to excise hPTH(1-34) from the chimeric protein CATPH34, 239 μl of deionized water, 1.32 μl of 1M CaCl$_2$ and 30 kU of Kex2-660 were added to 60 μl taken from the eluate from Reference Example 2, and the mixture was heated at 37° C. for one hour. After the reaction the appearing peaks were examined for amino acid analysis, and the amino acid composition was found to match that of hPTH (1-34) (FIG. 21).

That is, it was shown that no other protease activity is detected even with an absence of urea in the reaction solution, and thus that Kex2-660 can be used for excision of hPTH(1-34) from chimeric proteins. Furthermore, Kex2-660 is able to excise desired proteins even when the chimeric proteins have different protective peptides and cleavage site regions, and thus it has wide industrial application.

Example 7

Excision of hPTH(1-34) from chimeric protein βGal-117S4HPPH34

To 250 ml of the BGal-117S4HPPH34 inclusion bodies suspension (160 g/L) prepared in Reference Example 3 there were added 100 ml of 1M Tris/HCl (pH 8.2), 50 ml of 5M NaCl, 500 ml of deionized water and 900 g of urea, and after stirring to dissolution for 30 minutes in a constant temperature bath at 30° C., the solution was diluted with warmed deionized water to 5 L at 30° C.

To this there was gently added 50 ml of a 250 mM CaCl$_2$ solution while stirring, and then Kex2-660 was added to 20 kU/ml. After 2 hours, 7 g of hPTH(1-34) was excised at an efficiency of over 90%. The amount of Kex2-660 used was less than 1/20,000 of the chimeric protein (weight ratio), and this demonstrated that hPTH(1-34) was efficiently excised from the chimeric protein.

Example 8

Expression of secretory Kex2 derivatives in *Candida boidinii*

The results of Example 1 demonstrated that Kex2-660 undergoes no notable autolysis in culture solution. Thus, greater yields may be expected by using more efficient expression systems. We therefore attempted to produce Kex2-660 in an expression system using the methanol-utilizing yeast *Candida boidinii* as the host.

Figure 22:
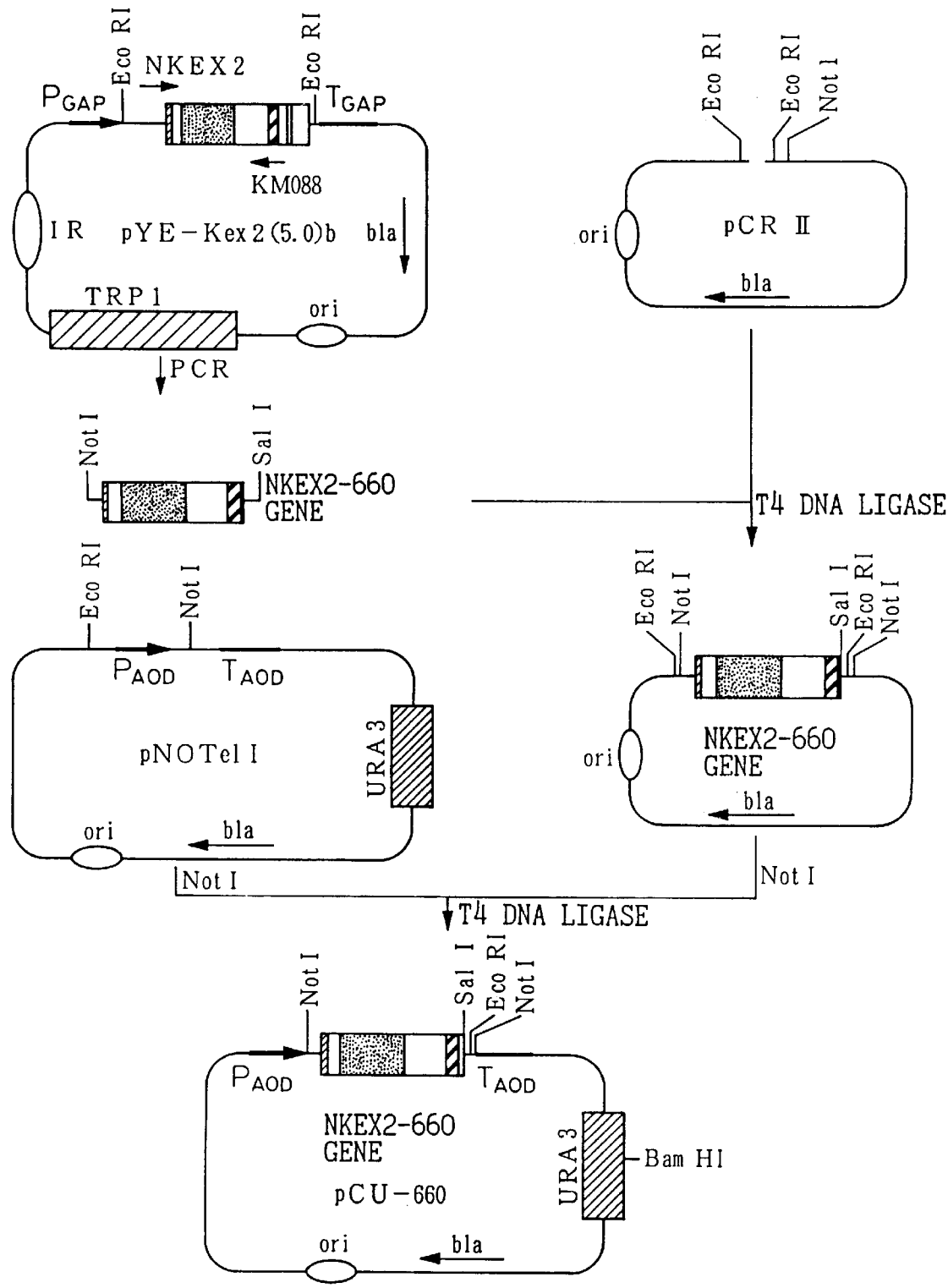
FIG. 22 shows a process for constructing plasmid pCU660 which expresses Kex2-660.

1) Construction of expression plasmid using *Candida boidinii* (FIGS. 11 and 22)

The NKEX2-660 gene was constructed by the PCR in the same manner as Example 1, 1), except that NKEX2 (SEQ ID NO.41) and KM088 were used as the primers. NKEX2 contains the nucleotide sequence of the restriction enzyme NotI site (underlined) at the 5'-end, and includes the sequence of bases −107 to −132 upstream from the initial methionine of the KEX2 gene (FIG. 11). The NKEX2-660 gene (the KEX2 gene with 132 base pairs of the 5' untranslated region of the KEX2 gene) was cloned in PCRII and then excised using restriction enzyme NotI. The NotI DNA fragment containing the NKEX2-660 gene was inserted at the NotI site of plasmid pNOTeII under promoter control to allow expression of the KEX2-660 gene, to thus construct pCU660 (FIG. 22).

Figure 23:
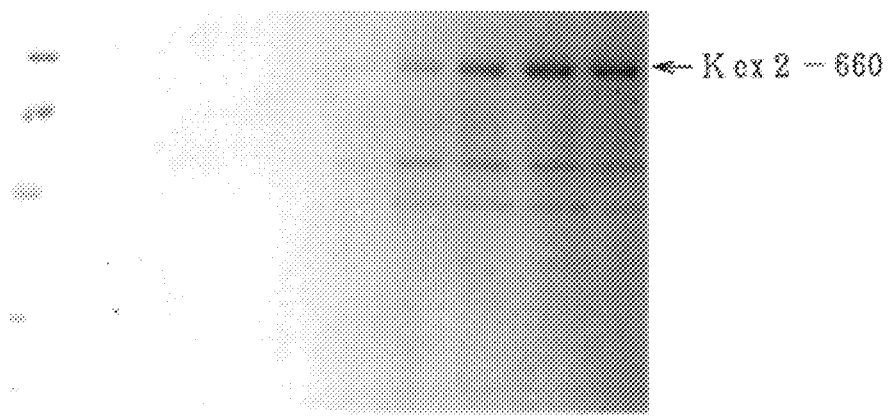
FIG. 23 is a photograph of SDS-PAGE which shows the secretion of Kex2-660 in culture supernatants for different culturing times of TK62/pCU660#10.

2) Production of secretory Kex2 derivative with *Candida boidinii* (FIG. 23)

Plasmid pCU660 which had been digested with restriction enzyme BamHI on the URA3 gene and in linear form was introduced into TK62, and the transformed strains TK62/pCU660 were selected. Twenty TK62[pCU660] strains (#1 to #20) were then cultured at 27° C. with shaking in BMGY medium. After 2 days, approximately 10 OD·ml of the preculturing solution was transferred into 1 ml of BMMY medium and further cultured at 27° C. with shaking. After 30 hours, the Kex2 activity of the culture supernatant was measured. The 5 strains with the highest activity were cultured in the same manner, and TK62[pCU660]#10 which had reproducible high Kex2 activity was selected and cultured in a fermenter.

After transferring 1 ml of glycerol-frozen stock TK62 [pCU660]#10 into a 300 ml Erlenmeyer flask containing 25 ml of YPD medium, it was precultured at 27° C. for 16 hours. A 10.5 ml portion of the preculture solution (OD600= 38) was transferred into 2 L of YPGM culturing medium, and a 5 L fermenter (Model KMJ-5B-4U-FP, of Mitsuwa Rika) was used for culturing at 27° C. The aeration volume was 4 L/min and the stirring speed was adjusted so that the amount of dissolved oxygen remained over 2.5 ppm. The methanol, glycerol and nitrogen source (5% (w/v) yeast extract, 10% (w/v) peptone, 6.7% (v/v) YNB w/o AA; 1/25 volume/addition) were supplemented as appropriate.

The pH was controlled to remain above pH 5.5 by adding 7.5% (v/v) ammonia water. An antifoaming agent (Disfoam CC-222, Nihon Yushi, KK.) was added at 0.5 ml/L, at the start of culturing and was added thereafter as necessary. The results of SDS-PAGE for the culture supernatant at each culturing time are shown in FIG. 23. The OD600 after 48 hours of culturing was 353, and this culturing produced about 2800 MU of Kex2-660 (corresponding to about 340 mg) per 1 L of culture supernatant.

This yield is capable of excision of 200 g of hPTH(1-34) in Example 7, and thus it was shown that the Kex2 derivative of the invention can be practically used for excision of desired peptides from chimeric proteins on an industrial scale.

Example 9

Expression of secretory Kex2 derivative in *Saccharomyces cerevisiae* (2)

In Example 1 it was demonstrated that the yields of Kex2 proteases lacking the C-terminal region (Kex2-660 and Kex2-679) were notably higher than those of Kex2-614, Kex2-699 and Kex2-688. In this example, additional Kex2 proteases lacking the C-terminal region (Kex2-630, Kex2-640, Kex2-650 and Kex2-682) were constructed, to further investigate the relationship between the C-terminal region and Kex2 protease yields.

1) Construction of secretory Kex2 derivative-expressing plasmids

The secretory Kex2 genes were constructed by the method in Example 1, 1). Specifically, the primer sequences KM100 (SEQ ID NO.42), KM102 (SEQ ID NO.43), KM103 (SEQ ID NO.44) and KM104 (SEQ ID NO.45) have nucleotide sequences which are antisense strands to sequences in which the translation termination codon TAA is added directly after the 630th, 640th, 650th and 682nd amino acids from the N-terminus, respectively.

Construction of EcoRI-SalI DNA fragments coding for the secretory Kex2 derivative genes and the expression vectors containing them was accomplished by the method in Example 1, 1). The polypeptides from the N-terminus of Kex2 protease to the 630th, 640th, 650th and 682nd amino acids were named Kex2-630, Kex2-640, Kex2-650 and Kex2-682, and the genes coding for them were named KEX2-630, KEX2-640, KEX2-650 and KEX2-682, respectively.

Figure 25:
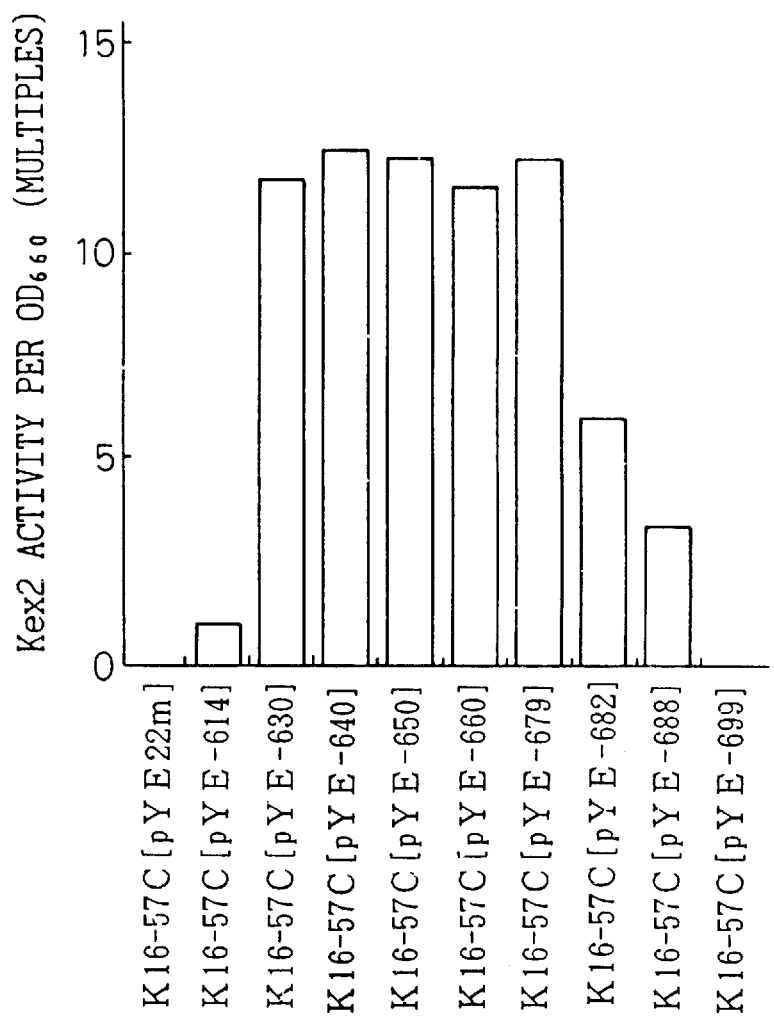
FIG. 25 is a graph comparing yield of each secretory Kex2 derivative per OD660 of culture based on Kex2 activities using a synthetic substrate. The yields of each of the secretory Kex2 derivatives are given with the yield of K16-57C[pYE22-614] as 1.
Figure 26:
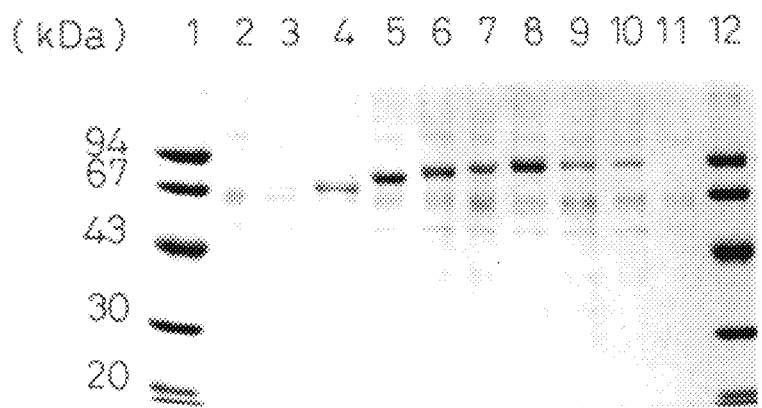
FIG. 26 is a photograph of SDS-PAGE which gives a comparison of yields per 200 μl of culture supernatant of secretory Kex2 derivatives. Lanes 1 and 12 are developed from molecular weight markers, and lanes 2 through 11 from concentrates of culture supernatants of K16-57C[pYE-22m], K16-57C[pYE22-614], K16-57C[pYE22-630], K16-57C[pYE22-640], K16-57C[pYE22-650], K16-57C [pYE22-660], K16-57C[pYE22-679], K16-57C[pYE22-682], K16-57C[pYE22-688] and K16-57C[pYE22-699]. In this representation of the electropherogram, the numbers to the left of lane 1 indicate the size (kDa) of the molecular weight markers.

2) Transformation and production of secretory Kex2 derivatives (see FIGS. 25 and 26)

Plasmids (pYE-630, pYE-640, pYE-650 and pYE-682) were introduced into strain K16-57C to obtain strains K16-57C[pYE-630], K16-57C[pYE-640], K16-57C[pYE-650] and K16-57C[pYE-682]. These transformants were then cultured, with the secretory Kex2 derivative-producing strains prepared in Example 1, 2), and the Kex2 yields (amount of Kex2 secreted into the culture medium) were determined by measurements of Kex2 activity in the culture supernatants and SDS-PAGE of the culture supernatant concentrates.

The colonies were inoculated into YCDP medium and then cultured at 30° C. with shaking to prepare cells in the logarithmic growth phase. These cells were subcultured in YCDP medium until the OD660 absorbance reached approximately 0.02, and then further cultured for about 16 hours at 30° C. The results of Kex2 activity measurement are shown in FIG. 25, and the results of SDS-PAGE are shown in FIG. 26.

The Kex2 activities per OD660 in culture supernatant for K16-57C[pYE-630], K16-57C[pYE-640], K16-57C[pYE-650], K16-57C[pYE-660] and K16-57C[pYE-679] were roughly 12 times that of K16-57C[pYE-614], thus showing no difference in Kex2 yields for the range of KEX2-630 to KEX2-679.

In addition, the Kex2 yields for K16-57C[pYE-682] and K16-57C[pYE-688] were, respectively, 6 times and 3.4 times that of K16-57C[pYE-614], i.e. they were lower the longer the C-terminal region (FIG. 25). No Kex2 activity was detected in the culture supernatants of K16-57C[pYE-22m] and K16-57C[pYE-699].

Also, the results of SDS-PAGE demonstrated that the yields for Kex2-630, Kex2-640, Kex2-650, Kex2-660, Kex2-679, Kex2-682 and Kex2-688 were also greater than for Kex2-614, similar to the Kex2 activities (FIG. 26).

Example 10

Expression of secretory Kex2 derivative in *Pichia pastoris*

The results of Example 8 showed that the secretory Kex2 derivative Kex2-660 can be produced in large amounts in an expression system using *Candida boidinii* as the host. The possibility of producing Kex2-660 with other methylotrophic yeast was investigated using an expression system with *Pichia pastoris* as the host (Pichia Expression Kit, Invitrogen Co.).

Figure 27:
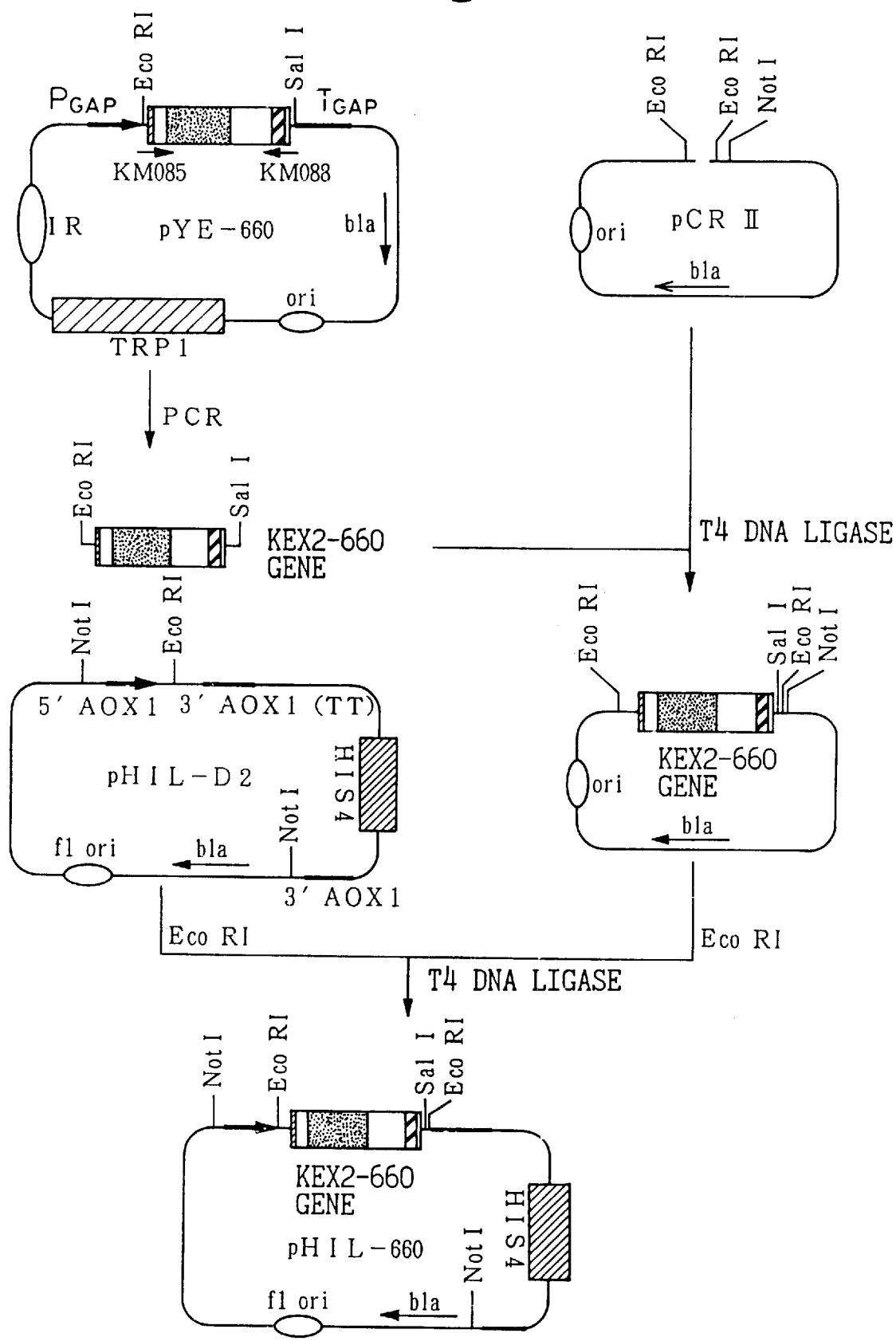
FIG. 27 shows a process for the construction of Kex2-660 expression plasmid pHIL-660 for a host Pichia pastoris.

1) Construction of secretory Kex2 derivative-expressing plasmid in *Pichia pastoris* host (see FIGS. 11 and 27)

A PCR reaction was conducted using plasmid pYE-660, digested with restriction enzyme EcoRI and in linear form, as the template and KMO85 (SEQ ID NO.36) and KM088 (SEQ ID NO.37) as primers. The reaction purification product was cloned in pCRII (Invitrogen Co.). The resulting plasmid was digested with restriction enzyme EcoRI, to obtain a DNA fragment consisting of the KEX2-660 gene with the restriction enzyme EcoRI site at both ends.

The DNA fragment containing the KEX2-660 gene was inserted at the restriction enzyme EcoRI site of plasmid pHIL-D2 (Pichia Expression Kit), to obtain plasmid pHIL-660 having the KEX2-660 gene inserted in an orientation allowing its expression under AOX promoter (FIG. 27).

2) Production of secretory Kex2 derivative in *Pichia pastoris*

A fragment containing the KEX2-660 gene obtained by digesting plasmid pHIL-660 with restriction enzyme NotI was introduced into *Pichia pastoris* GS115 (his$^-$, AOX$^+$, Pichia Expression Kit), and the GS115[pHIL-660] transformants which grew in medium containing no histidine were selected. From these were obtained 5 GS115[pHIL-660]

(AOX⁻) strains which could not grow with methanol alone as the carbon source. These were then cultured in BMMY medium, to obtain GS115[pHIL-660] #23 which had the greatest yield of Kex2 production.

The Kex2 yield of GS115[pHIL-660] #23 was then examined. First, a colony was seeded into 10 ml of BMGY medium and cultured at 30° C. for 2 days with shaking. Cells obtained by centrifugation of 10 ml of the culture medium were suspended in 2 ml of BMMY medium and further cultured at 25° C. for 2 days with shaking, after which the Kex2 activity of the culture supernatant was measured. As a result, the production of Kex2-660 was found to be about 1350 KU (corresponding to about 160 μg) per 1 ml of culture medium.

Thus it was demonstrated that Kex2-660 can be produced in large amounts even in an expression system in which the host is *Pichia pastoris*, methylotrophic yeast other than *Candida boidinii*.

FIG. 27 shows the method of constructing the Kex2-660-expressing plasmid pHIL-660 with *Pichia pastoris* as the host.

We claim:

1. A process for production of a protein with Kex2 protease enzyme activity, wherein said protein has a shortened amino acid sequence whose N-terminus is Met at amino acid position 1 and whose C-terminus is an amino acid between the 630th amino acid (inclusive) and the 682nd amino acid (inclusive) of SEQ ID NO.: 1, or has a shortened amino acid sequence whose N-terminus is Met at amino acid sequence 1 and whose C-terminus is an amino acid between the $630^{th}$ amino acid (inclusive) and the $682^{nd}$ amino acid (inclusive) of SEQ ID NO.: 1, wherein the amino acid sequence is modified by substitution, deletion or addition of one or more amino acids in a region in said shortened amino acid sequence from amino acid 615 to the C-terminus, said process comprising the steps of:

culturing methylotrophic yeast cells transformed with yeast expression vector comprising a DNA coding for said protein; and recovering the protein from the culture.

2. A process according to claim 1, wherein the methylotrophic yeast is a yeast belonging to a genus selected from the group consisting of the genera Pichia, Hansenula and Candida.

3. A process according to claim 2, wherein the methylotrophic yeast is selected from the group consisting of the species *Pichia pastoria, Hansenula polymorpha* and *Candida boidinii*.

4. A process for production of a protein with Kex2 protease enzyme activity having a shortened amino acid sequence whose N-terminus is Met at amino acid position 1 and whose C-terminus is an amino acid between the 630th amino acid (inclusive) and the 682nd amino acid (inclusive) of SEQ ID NO: 1, comprising the step of:

culturing methylotrophic yeast cells transformed with an yeast expression vector comprising a DNA coding for said protein; and recovering the protein from the culture.

5. A process according to claim 4, wherein the methylotrophic yeast is a yeast belonging to a genus selected from the group consisting of the genera Pichia, Hansenula and Candida.

6. A process according to claim 5, wherein the methylotrophic yeast is selected from the group consisting of the species *Pichia pastoris, Hansenula polymorpha* and *Candida boidinii*.

7. A process according to claim 4, wherein said protein has a shortened amino acid sequence whose N-terminus is Met at amino acid sequence 1 and whose C-terminus is an amino acid between the $630^{th}$ amino acid (inclusive) and the $682^{nd}$ amino acid (inclusive) of SEQ ID NO.: 1, wherein the amino acid sequence is modified by substitution, deletion or addition of one or more amino acids in a region in said shortened amino acid sequence from amino acid 615 to the C-terminus.

* * * * *